(12) United States Patent
Medoff et al.

(10) Patent No.: US 9,453,250 B2
(45) Date of Patent: *Sep. 27, 2016

(54) PROCESSING MATERIALS

(71) Applicant: Xyleco, Inc., Woburn, MA (US)

(72) Inventors: Marshall Medoff, Brookline, MA (US); Thomas Craig Masterman, Rockport, MA (US)

(73) Assignee: Xyleco, Inc., Wakefield, MA (US)

( * ) Notice: Subject to any disclaimer, the term of this patent is extended or adjusted under 35 U.S.C. 154(b) by 137 days.

This patent is subject to a terminal disclaimer.

(21) Appl. No.: 14/224,381

(22) Filed: Mar. 25, 2014

(65) Prior Publication Data

US 2014/0206044 A1 Jul. 24, 2014

Related U.S. Application Data

(63) Continuation of application No. 12/949,044, filed on Nov. 18, 2010, now Pat. No. 8,691,526.

(60) Provisional application No. 61/296,673, filed on Jan. 20, 2010, provisional application No. 61/296,658, filed on Jan. 20, 2010.

(51) Int. Cl.
| | |
|---|---|
| *C12P 1/00* | (2006.01) |
| *C12P 19/02* | (2006.01) |
| *C12P 19/14* | (2006.01) |
| *B01D 3/00* | (2006.01) |
| *C12P 7/02* | (2006.01) |
| *C12P 7/10* | (2006.01) |

(52) U.S. Cl.
CPC ............. *C12P 19/14* (2013.01); *B01D 3/001* (2013.01); *B01D 3/002* (2013.01); *C12P 7/02* (2013.01); *C12P 7/10* (2013.01); *C12P 19/02* (2013.01); *C12P 2203/00* (2013.01); *Y02E 50/16* (2013.01)

(58) Field of Classification Search
CPC ........ C12P 1/00; C12P 19/02; C12P 2203/00
See application file for complete search history.

(56) References Cited

U.S. PATENT DOCUMENTS

| | | | |
|---|---|---|---|
| 4,176,522 A | 12/1979 | Holtzapple et al. | |
| 4,426,450 A | 1/1984 | Donofrio | |
| 5,426,024 A | 6/1995 | Flores-Cotera et al. | |
| 5,853,589 A | 12/1998 | Desjardins et al. | |
| 6,455,306 B1 | 9/2002 | Goldstein et al. | |
| 7,807,419 B2 | 10/2010 | Hennessey et al. | |
| 8,691,526 B2 * | 4/2014 | Medoff ............... | B01D 3/001 435/183 |
| 2003/0044951 A1 | 3/2003 | Sporleder et al. | |
| 2007/0217954 A1 | 9/2007 | Powell et al. | |
| 2008/0193991 A1 | 8/2008 | Allen et al. | |
| 2008/0202504 A1 | 8/2008 | Hilst | |

FOREIGN PATENT DOCUMENTS

| | | |
|---|---|---|
| BE | 414030 | 3/1936 |
| CN | 2110640 | 7/1992 |
| CN | 2142464 | 9/1993 |
| CN | 2334762 | 8/1999 |
| CN | 2762897 | 3/2006 |
| CN | 1844347 | 10/2006 |
| DE | 2310256 | 9/1973 |
| EP | 1728853 | 12/2006 |
| EP | 2112226 | 10/2009 |
| GB | 470898 | 8/1937 |
| JP | S6178390 | 4/1986 |
| JP | 1017701 | 1/1989 |
| JP | 2000139221 | 5/2000 |
| JP | 2006121954 | 5/2006 |
| JP | 2009045037 | 3/2009 |
| JP | 2009183264 | 8/2009 |
| WO | 2008047679 | 4/2008 |
| WO | 2008073186 | 6/2008 |
| WO | 2009045651 | 4/2009 |
| WO | 2009120731 | 10/2009 |

OTHER PUBLICATIONS

Japanese Office Action, Corresponding Japanese Patent Application No. 2012-549990, dated Aug. 4, 2015, 3 pages.
Office Action—Corresponding Japanese Patent Application No. 2012-549990, dated Jan. 13, 2015, 3 pages.
Smith et al., Irradiation Enhancement of Biomass Conversion, Radiat. Phys. Chem., vol. 25, No. 1-3, p. 27-33, 1985.
Rudolf A. et al., "Simultaneous Saccharification and Fermentation of Steam-Pretreated Bagasse Using Saccharomyces cerevisiae TMB3400 and Pichia stipitus CBS6054," Biotechnology and Bioengineering, Mar. 1, 2008, vol. 99, No. 4, Mar. 1, 2008, pp. 783-790.
Marques et al., "Conversion of Recycled Paper Sludge to Ethanol by SHF and SSF using Pichia stipitis," Biomass and Bioenergy, Pergamon, Oxford, GB, vol. 32, No. 5, May 1, 2008, pp. 400-406.
Van Zyl Willem H et al., "Consolidated Bioprocessing for Bioethanol Production Using Saccharomyces Cereviside," Advances in Biochemical Engineering, Biotechnology, Springer, Berlin, DE, Jan. 1, 2007, pp. 205-235.
Fujita et al., "Synergistic Saccharification, and Direct Fermentation to Ethanol, of Amorphous Cellulose by Use of an Engineered Yeast Strain Codisplaying Three Types of Cellulolytic Enzyme," Applied and Environmental Microbiology, American Society for Microbiology, US, vol. 70, No. 2, Feb. 1, 2004, pp. 1207-1212.
Eklund et al., "Simultaneous Saccharification and Fermentation of Steam-Pretreated Willow," Enzyme and Microbial Technology, 1995, vol. 17, p. 255-259.

(Continued)

*Primary Examiner* — Ruth Davis
(74) *Attorney, Agent, or Firm* — Leber Patent Law P.C.

(57) ABSTRACT

Biomass feedstocks (e.g., plant biomass, animal biomass, and municipal waste biomass) are processed to produce useful products, such as fuels. For example, systems are described that can convert feedstock materials to a sugar solution, which can then be fermented to produce ethanol. Biomass feedstock is saccharified in a vessel by operation of a jet mixer, the vessel also containing a liquid medium and a saccharifying agent.

16 Claims, 15 Drawing Sheets

(56) References Cited

OTHER PUBLICATIONS

Dasari et al., "High-Solids Saccharification and Viscosity Studies in a Scraped Surface and Bio-Reactor", B.Tech., Osmania University, India, 2004, Dissertation approved Mar. 27, 2008.
ISR for International Application No. PCT/US2010/057272, mailed Jun. 20, 2011, 3 pages.
Written Opinion for International Application No. PCT/US2010/057272, mailed Jun. 20, 2011, 7 pages.
ISR and Written Opinion for PCT/US2010/35328, US as ISA, mailed Jun. 29, 2010, 5 pages
ISR and Written Opinion for PCT/US2010/035315, EPO as ISA, mailed Apr. 2, 2011, 18 pages.
Written Opinion for SG Patent Application No. 201204737-9, mailed Apr. 15, 2013, 12 pages.
CN search report—corresponding application No. 2010800616598, dated Jul. 3, 2013, 1 page.

* cited by examiner

PROCESSING MATERIALS

RELATED APPLICATIONS

This application is a continuation of U.S. Ser. No. 12/949,044, filed Nov. 18, 2010, which claimed priority to U.S. Provisional Application Ser. No. 61/296,673, filed Jan. 20, 2010, and U.S. Provisional Application Ser. No. 61/296,658, filed Jan. 20, 2010. The complete disclosure of each of these applications is hereby incorporated by reference herein.

BACKGROUND

Cellulosic and lignocellulosic materials are produced, processed, and used in large quantities in a number of applications. Often such materials are used once, and then discarded as waste, or are simply considered to be waste materials, e.g., sewage, bagasse, sawdust, and stover.

Various cellulosic and lignocellulosic materials, their uses, and applications have been described in U.S. Pat. Nos. 7,307,108, 7,074,918, 6,448,307, 6,258,876, 6,207,729, 5,973,035 and 5,952,105; and in various patent applications, including "FIBROUS MATERIALS AND COMPOSITES," PCT/US2006/010648, filed on Mar. 23, 2006, AND "FIBROUS MATERIALS AND COMPOSITES," U.S. Patent Application Publication No. 2007/0045456.

SUMMARY

Processes are disclosed herein for producing a product by multiple bioprocesses which are all conducted in a single tank.

Some processes include saccharifying or liquifying a material, e.g., a cellulosic or lignocellulosic feedstock, by converting the cellulosic portion of the material to low molecular weight sugars, e.g., using an enzyme, and then converting the resulting sugars to a product, e.g., by fermentation and distillation. In some implementations processes include utilizing dispersing systems to disperse a fibrous and/or particulate feedstock in a liquid medium and mixing systems, e.g., low shear systems such as jet mixing systems, to mix the material in the tank. In some implementations, the dispersing system includes a chamber and, within the chamber, a rotating member which draws the feedstock and liquid medium into the chamber axially and expels a dispersion of the feedstock in the medium from the chamber radially.

The processes disclosed herein can utilize low bulk density materials, for example cellulosic or lignocellulosic feedstocks that have been physically pretreated to have a bulk density of less than about 0.75 g/cm$^3$, e.g., less than about 0.7, 0.65, 0.60, 0.50, 0.35, 0.25, 0.20, 0.15, 0.10, 0.05, or less, e.g., less than 0.025 g/cm$^3$. Such materials can be especially difficult to disperse in liquids, e.g., with water or a solvent system for saccharification, fermentation, or other processing. Due to their low bulk density, the materials tend to float on the surface of the liquid rather than being wetted out and dispersed into the liquid. In some cases, the materials can be hydrophobic, highly crystalline, or otherwise difficult to wet. At the same time, it is desirable to process the feedstock in a relatively high solids level dispersion, in order to obtain a high final concentration of sugar in the saccharified material, or a high concentration of the desired product after processing (e.g., of ethanol or other alcohol(s) after fermentation). In some cases, utilizing the methods described herein the solids level of the dispersion during processing can be, for example, at least 10, 15, 20, 22.5, 25, 27.5, 30, 35, 40, 45, or even at least 50 percent by weight dissolved solids. For example, the solids level can be from about 10 to 50%, e.g., about 10-40%, 10-30%, or 10-20%.

The processes herein also, in some cases, allow enzymes and/or microorganisms used in the process to be reused in a batch process, or used over a long period of time in a continuous process.

In one aspect, the invention features a method that includes saccharifying a biomass feedstock in a liquid medium in a vessel, e.g., a tank, to form a sugar solution, and converting the sugar solution to a product, e.g., an alcohol, in the same vessel, utilizing an enzyme and/or a microorganism.

Some implementations include one or more of the following features. Converting can include fermentation. The method can further include distillation, e.g., vacuum distillation. Distillation may be performed at a vacuum of less than 70 Torr. Distillation may be performed at ambient temperature.

In some cases, the feedstock has a low bulk density, e.g., a bulk density of less than about 0.5 g/cm$^3$. The liquid medium may include water, and the saccharifying agent can include an enzyme. The feedstock may include a cellulosic or lignocellulosic material.

The method may include additional steps. For example, the method may further include mixing with a jet mixer during saccharification. Mixing, with a jet mixer or other mixer, may also be performed during distillation. The method may also include monitoring a glucose level of a mixture of the feedstock, the liquid medium and the saccharifying agent during saccharification. In some cases, the method further includes adding additional feedstock and saccharifying agent to the vessel during saccharification and dispersing the feedstock in the medium using the dispersing system. The method may further include adding an emulsifier or surfactant to the mixture in the vessel.

In another aspect, the invention features a system that includes a tank, a delivery system configured to deliver a biomass feedstock, a saccharification agent, and a liquid medium to the tank, a mixer configured to mix the delivered biomass feedstock and saccharifying agent, and a vacuum distillation system in communication with the tank, configured to distill a product from the contents of the tank.

Some implementations may include one or more of the following features. The system can further include a delivery device configured to inoculate the contents of the tank with a microorganism. The system can further include an oxygen monitor configured to monitor the oxygen level of the contents of the tank. The mixer can be or include a jet mixer. The delivery system can be configured to deliver the biomass feedstock and liquid medium to the tank in the form of a dispersion.

By performing multiple processing steps, e.g., saccharification, fermentation and distillation, in a single tank, process times and cost are reduced and the process is simplified. Also, capital costs are generally lower than for a multi-tank processing facility.

In some cases, the systems described herein, or components thereof, may be portable, so that the system can be transported (e.g., by rail, truck, or marine vessel) from one location to another. Such mobile processing is described in U.S. Ser. No. 12/374,549 and International Application No. WO 2008/011598, the full disclosures of which are incorporated herein by reference.

Exemplary products that can be produced by employing the methods described herein include hydrocarbons, proteins, alcohols (e.g., a monohydric alcohols or a dihydric alcohols), such as ethanol, n-propanol or n-butanol, carboxylic acids, such as acetic acid or butyric acid, salts of a carboxylic acid, a mixture of carboxylic acids and salts of carboxylic acids and esters of carboxylic acids (e.g., methyl, ethyl and n-propyl esters), ketones, aldehydes, alpha, beta unsaturated acids, such as acrylic acid, olefins, such as ethylene, and mixtures of any of these. Specific examples include ethanol, propanol, propylene glycol, butanol, 1,4-butanediol, 1,3-propanediol, methyl or ethyl esters of any of these alcohols, methyl acrylate, methylmethacrylate, lactic acid, propionic acid, butyric acid, succinic acid, 3-hydroxypropionic acid, a salt of any of the acids and a mixture of any of the acids and respective salts. These and other products are described in U.S. Ser. No. 12/417,900, the disclosure of which is incorporated by reference herein.

Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

All publications, patent applications, patents, and other references mentioned herein or attached hereto are incorporated by reference in their entirety for all that they contain.

DETAILED DESCRIPTION

Figure 1:
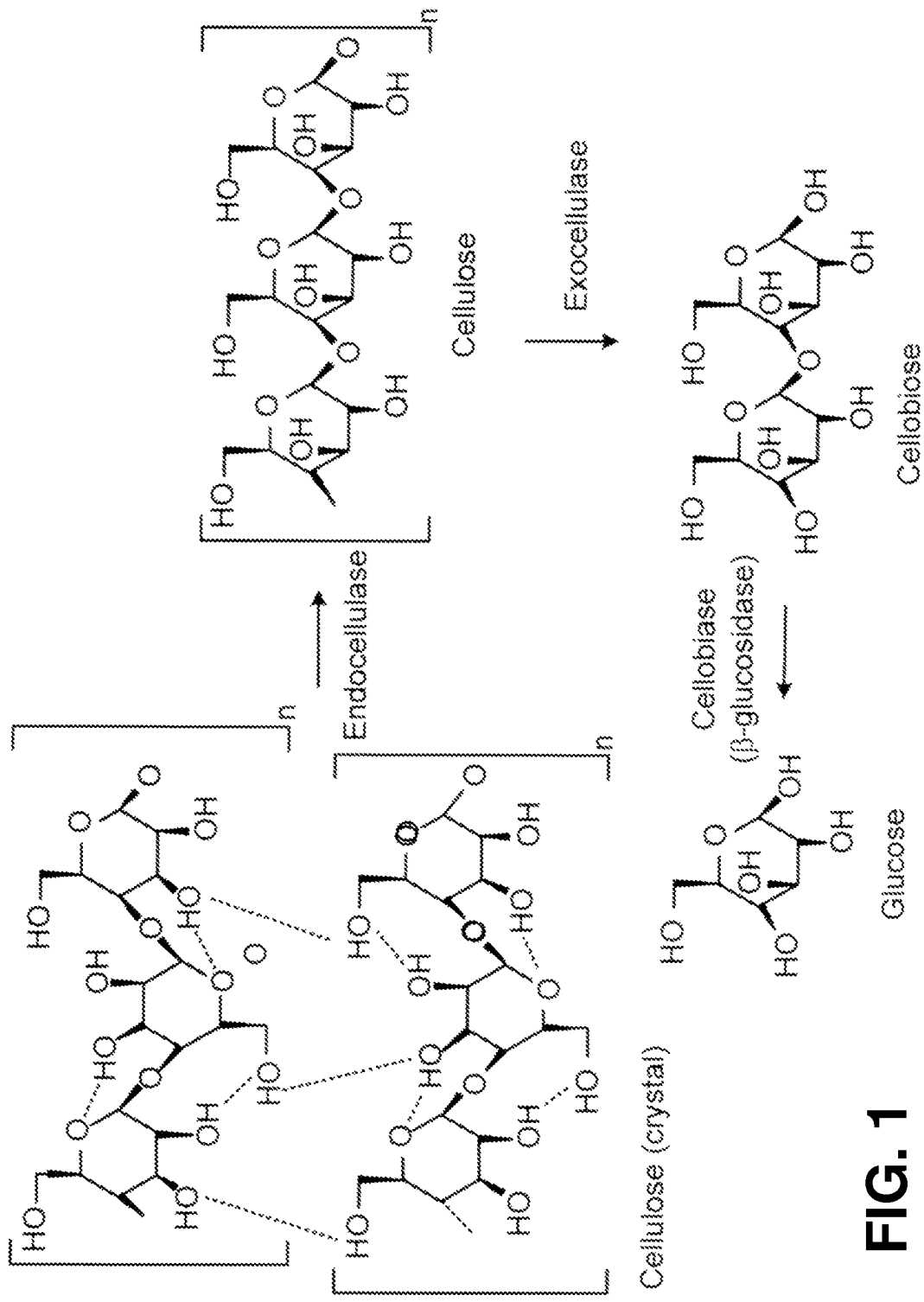
FIG. 1 is a diagram illustrating the enzymatic hydrolysis of cellulose to glucose.

Glucan- and/or xylan-containing materials, for example cellulosic and lignocellulosic materials such as Using the methods described herein, biomass (e.g., plant biomass, animal biomass, paper, and municipal waste biomass) can be converted intoprocessed to produce useful intermediates and products such as organic acids, salts of organic acids, anhydrides, esters of organic acids and fuels, e.g., fuels for internal combustion engines or feedstocks for fuel cells. those described herein. Systems and processes are described herein that can use as feedstock materials cellulosic and/or lignocellulosic materials that are readily abundant available, but often can be difficult to process cellulosic or lignocellulosic materials, e.g., municipal waste streams and waste paper streams, such as streams that include newspaper, kraft paper, corrugated paper or mixtures of these. Generally, if required, materials can be physically treated for processing and/or after processing, often by size reduction. If it is necessary to reduce the recalcitrance of the material, the physically processed processes such as fermentation. Many of the processes described herein can effectively lower the recalcitrance level of the feedstock, making it easier to process, such as by bioprocessing (e.g., with any microorganism described herein, such as a homoacetogen or a heteroacetogen, and/or any enzyme described herein), thermal processing (e.g., gasification or pyrolysis) or chemical methods (e.g., acid hydrolysis or oxidation). Biomass feedstock can be treated or processed using one or more of any of the methods described herein, such as mechanical treatment, chemical treatment, radiation, sonication, oxidation, pyrolysis or steam explosion. The various treatment systems and methods can be used in combinations of two, three, or even four or more of these technologies or others described herein and elsewhere.

In order to convert the feedstock to a form that can be readily processed in an existing manufacturing plant, for example, a single cell protein plant, an enzyme manufacturing plant, or a fuel plant, e.g., a grain ethanol manufacturing facility The processes disclosed herein can utilize low bulk density materials, for example cellulosic or lignocellulosic feedstocks that have been physically pretreated to have a bulk density of less than about 0.75 g/cm$^3$, e.g., less than about 0.7, 0.65, 0.60, 0.50, 0.35, 0.25, 0.20, 0.15, 0.10, 0.05. or less, e.g., less than 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

In order to convert the feedstock to a form that can be readily processed, the glucan- or xylan-containing cellulose in the feedstock is hydrolyzed to low molecular carbohydrates, such as sugars, by a saccharifying agent, e.g., an enzyme or acid, a process referred to as saccharification. The low molecular weight carbohydrates can then be used, for example, in an existing manufacturing plant, such as a single cell protein plant, an enzyme manufacturing plant, or a fuel plant, e.g., an ethanol manufacturing facility.

The materials that include cellulose can be treated with the saccharifying agent by combining the material and the saccharifying agent in a liquid medium, e.g., a solvent such as an aqueous solution. Methods for dispersing the material in the liquid medium quickly and efficiently are discussed in detail below. Once the material has been dispersed in the medium, the saccharifying agent, material and liquid medium are mixed thoroughly, in some cases throughout saccharification. In some implementations, the material and/or the saccharifying agent are added incrementally rather than all at once. For example, a portion of the material can be added to the liquid medium, dispersed therein, and mixed with the saccharifying agent until the material is at least partially saccharified, at which point a second portion of the material is dispersed in the medium and added to the mixture. This process can continue until a desired sugar concentration is obtained.

Enzymes and biomass-destroying organisms that break down biomass, such as the cellulose and/or the lignin portions of the biomass, contain or manufacture various cellulolytic enzymes (cellulases), ligninases or various small molecule biomass-destroying metabolites. These enzymes may be a complex of enzymes that act synergistically to degrade crystalline cellulose or the lignin portions of biomass.

Examples of cellulolytic enzymes include: endoglucanases, cellobiohydrolases, and cellobiases (β-glucosidases). Referring to FIG. 1, a cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally cellobiase cleaves cellobiose to yield glucose. Suitable cellulases will be discussed herein in a later section.

The time required for complete saccharification will depend on the process conditions and the feedstock and enzyme used. If saccharification is performed in a manufacturing plant under controlled conditions, the cellulose may be substantially entirely converted to glucose in about 12-96 hours. If saccharification is performed partially or completely in transit, saccharification may take longer.

In some cases, saccharification is performed at a pH of about 4 to 7, e.g., about 4.5 to 6, or about 5 to 6.

It is generally preferred that the final concentration of glucose in the sugar solution be relatively high, e.g., greater than 10%, or greater than 15, 20, 30, 40, 50, 60, 70, 80, 90 or even greater than 95% by weight. This reduces the volume to be shipped, and also inhibits microbial growth in the solution. After saccharification, the volume of water can be reduced, e.g., by evaporation or distillation.

A relatively high concentration solution can be obtained by limiting the amount of medium, e.g., water, added to the feedstock with the enzyme. The concentration can be controlled, e.g., by controlling how much saccharification takes place. For example, concentration can be increased by adding more feedstock to the solution. Solubility of the feedstock in the medium can be increased, for example, by increasing the temperature of the solution, and/or by adding a surfactant as will be discussed below. For example, the solution can be maintained at a temperature of 40-50° C., 50-60° C., 60-80° C., or even higher.

Figure 2:
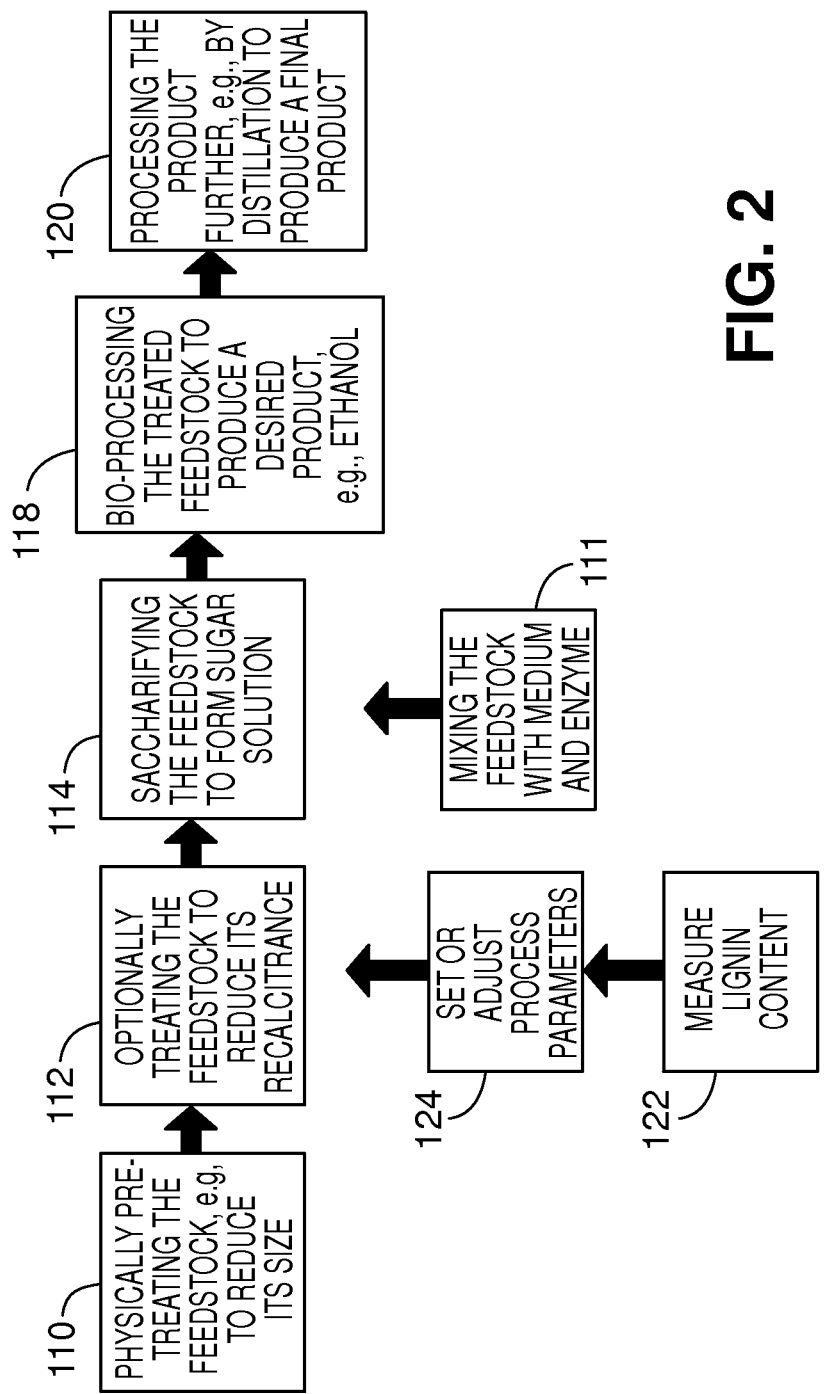
FIG. 2 is a flow diagram illustrating conversion of a feedstock to ethanol via production and fermentation of a glucose solution.

Referring to FIG. 2, a process for manufacturing an alcohol, e.g., ethanol, can include, for example, optionally physically pre-treating the feedstock, e.g., to reduce its size (step 110), before and/or after this treatment, optionally treating the feedstock to reduce its recalcitrance (step 112), and saccharifying the feedstock to form a sugar solution (step 114). Saccharification can be performed by mixing a dispersion of the feedstock in a liquid medium, e.g., water with an enzyme (step 111), as will be discussed in detail below. Without removing it from the tank in which it has been saccharified, the solution is next bio-processed to produce a desired product, e.g., ethanol (step 118), which is then processed further, e.g., by distillation (step 120). Preferably, distillation is performed in the same tank as saccharification and fermentation, e.g., using vacuum distillation. The individual steps of this process will be described in detail below. If desired, the steps of measuring lignin content (step 122) and setting or adjusting process parameters (step 124) can be performed at various stages of the process, for example just prior to the process step(s) used to change the structure of the feedstock, as shown. If these steps are included, the process parameters are adjusted to compensate for variability in the lignin content of the feedstock, as described in U.S. Provisional Application No. 61/151,724, filed on Feb. 11, 2009, the complete disclosure of which is incorporated herein by reference.

Figure 3:
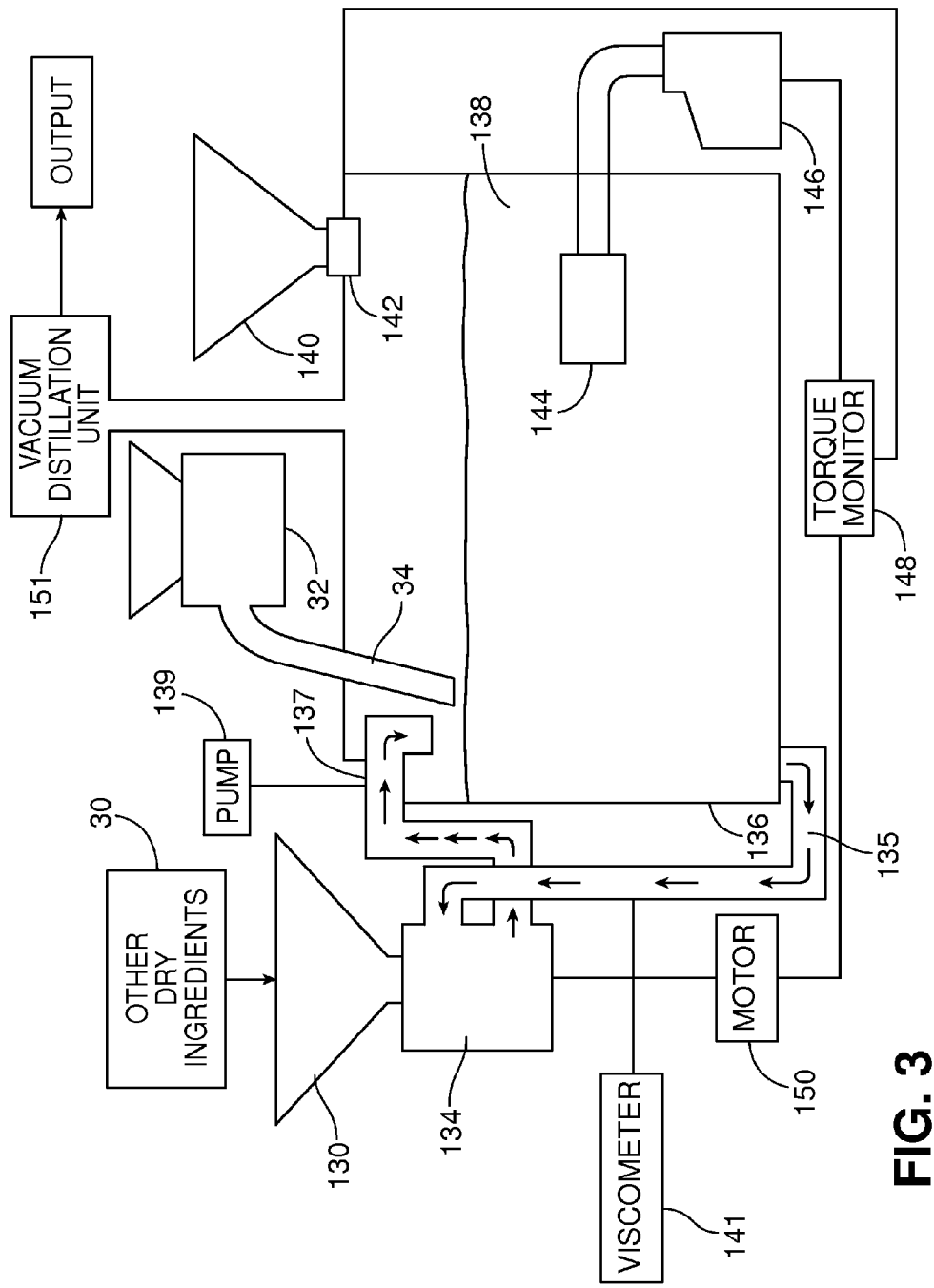
FIG. 3 is a diagrammatic illustration of a system for production of a product, e.g., ethanol, according to one embodiment.

The mixing step 111 and saccharifying step 114 can be performed using, for example, the system shown in FIG. 3. This system includes a tank 136, which initially contains a liquid medium and later contains a mixture 138 of liquid medium, feedstock and saccharifying agent. The liquid medium is delivered to the tank through a valved piping system (not shown). The system also includes a hopper 130, in communication with a dispersing unit 134. The hopper receives dry ingredients, such as yeast and nutrients, e.g., from a supply 30. Optionally, a vibrating device 36 may be associated with the hopper, to facilitate delivery of material from the hopper. The system also includes a dispersing unit 134. The liquid medium is drawn into the dispersing unit 134 from the tank, and returned to the tank by the dispersing unit via an outlet pipe 137. The opening of outlet pipe 137 may be above the liquid level, as shown, or may in some instances be submerged in the liquid in the tank. In some cases, depending on the type of dispersing unit used (as will be discussed below), the system may include a pump 139, e.g., a positive displacement pump, configured to circulate the liquid medium through the dispersing system, and/or a viscometer 141 to monitor the viscosity of the dispersion and activate the pump when the measured viscosity reaches a predetermined value.

Figure 12:
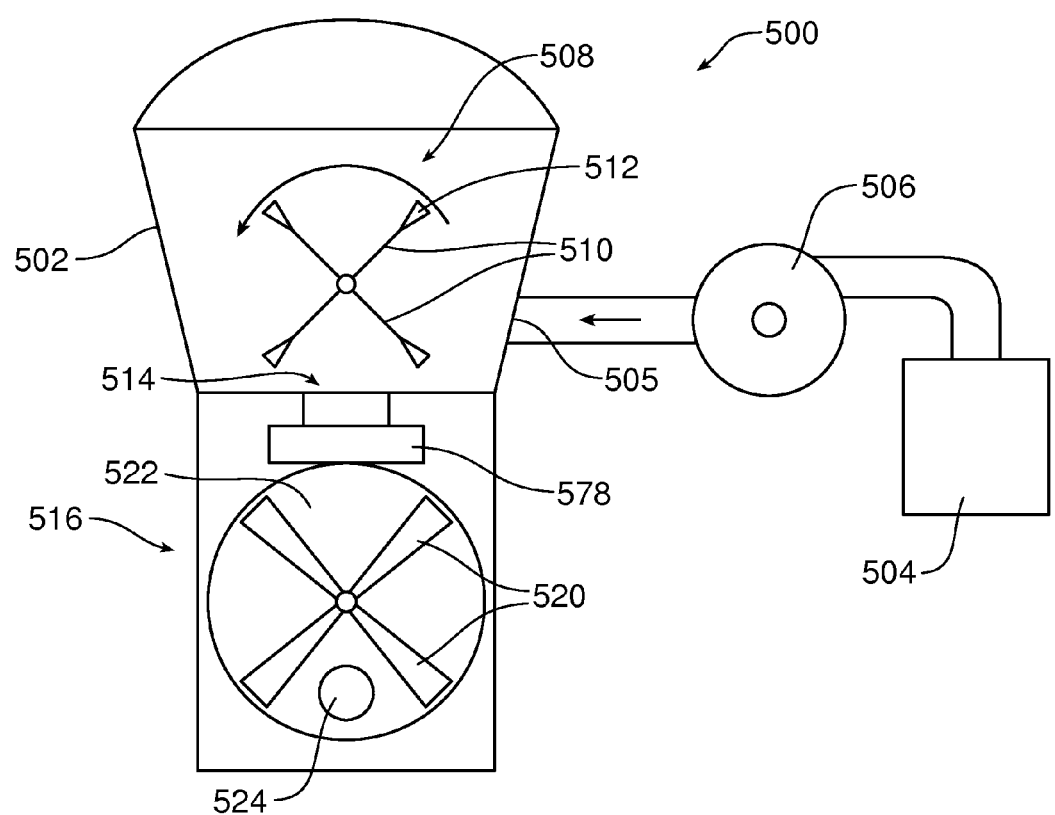
FIG. 12 is a diagrammatic view of a blower for delivering a biomass feedstock.

In the embodiment shown in FIG. 3, the feedstock is delivered to the surface of the liquid medium in the tank, e.g., via a delivery device 32 having a delivery conduit 34 (e.g., hose or pipe). The delivery device 32 may also be associated with a vibrating device 36, to facilitate flow of material into the device. The delivery device 32 may be, for example, a blower configured to blow fibrous and/or particulate material from a source to a location remote from the source through a hose, e.g., an insulation blower such as the FORCE 3 blower available from Intec, Frederick, Colo. An example of a blower 500 is shown schematically in FIG. 12. A hopper 502 of the blower 500 receives material from a material source 504, e.g., by drawing the material in through inlet 505 via a vacuum 506. Once in the hopper, the material is deagglomerated using a rotating device 508, which includes rotating arms 510 terminating in flexible paddles 512. The rotating device 508 also sweeps material down through an opening 514 to an airlock 516. Delivery of material to the airlock is metered by a plate or valve 518. The airlock 516 includes a plurality of rotating vanes 520 that define chambers 522. The lower portion of airlock 516 includes a passageway 524 through which air blows from a compressed air supply (not shown) into an outlet tube (e.g., delivery conduit 34, FIG. 3). The vanes sweep the material to the passageway in individual portions, which are blown into the outlet tube as soon as they are in place adjacent the passageway. The rotating vanes 520 rotate sufficiently slowly that each chamber is in position adjacent the passageway long enough so that both the portion of material and a certain amount of air are delivered into the outlet tube. Thus, alternating portions of air and material are delivered to the outlet tube. As the material passes down the outlet tube, which can be quite long, the material and air mix, aerating the material and keeping it moving smoothly through the outlet tube to the tank. The rate of rotation of the rotating members in the agitator and the airlock is geared together and can be varied by the user based on the feedstock, the length of the outlet tube, and other variables.

Alternatively, the material can be delivered to the surface of the liquid using other techniques, such as gravity feed or a screw conveyor.

In some implementations, the tank is provided with a flexible, air permeable cover, or other device configured to allow air to vent from the tank during delivery of the feedstock, while preventing feedstock from blowing out of the tank and/or contaminants from entering the tank.

As the feedstock material is delivered through delivery conduit 34 onto the surface of the liquid in the tank, liquid is discharged through outlet pipe 137 of the dispersing unit 134 onto the material. The discharged liquid wets the feedstock material, causing it to sink into the liquid, where it can be dispersed by the dispersing unit 134, preferably in combination with the mixing action of a jet mixer 144, discussed below.

It is generally preferred that the dispersing unit 134 and the jet mixer 144 are operating when the feedstock is delivered through the delivery conduit.

In an alternative embodiment, the hopper 130 receives feedstock that has been treated to reduce its size and optionally to reduce its recalcitrance (steps 110 and 112 above) by a feedstock pretreatment module 132, and the feedstock is delivered to the tank via hopper 130. The feedstock and liquid medium are drawn into the dispersing unit 134 from the tank, and the feedstock is dispersed in the liquid medium, e.g., water, by the action of the dispersing unit.

In both embodiments, a saccharifying agent is delivered to the tank from a hopper 140, which includes a metering device 142. The contents of the tank are mixed, e.g., by one or more jet mixers. A jet mixer 144 is represented diagrammatically in FIG. 3; examples of suitable jet mixers will be described in detail below, and are also described in U.S. Provisional Application No. 61/218,832, filed Jun. 19, 2009, the full disclosure of which is hereby incorporated by reference herein. The jet mixer produces a jet using a motor 146 that drives a pump and/or a rotor (not shown). The torque exerted by the motor 146 correlates with the solids level of the mixture in the tank, which in turn reflects the degree to which the mixture has saccharified. The torque is measured by a torque monitor 148, which sends a signal to a motor 150 that drives the conveyor 130 and also to the metering device 142 of the hopper 140. Thus, the supply of the treated feedstock and the enzyme can be interrupted and resumed as a function of the saccharification of the contents of the tank. The data measured by the torque monitor can also be used to adjust the jet mixer, e.g., to a lower RPM for a mixer that utilizes a rotor, or to a lower jet velocity for a pump-driven mixer. Instead of, or in addition to, the torque monitor, the system may include an Amp monitor (not shown) that measures the full load amperage of the motor. In some cases, the jet mixer may include a variable frequency drive (VFD) to allow the speed of the motor to be adjusted.

The system may also include a heat monitor (not shown) that monitors the temperature of the liquid medium and adjusts the feed rate of the feedstock and/or the mixing conditions in response to increases in temperature. Such a temperature feedback loop can be used to prevent the liquid medium from reaching a temperature that will denature the enzyme.

When one or more pumps are used in the systems described herein, it is generally preferred that positive displacement (PD) pumps be used, e.g., progressive cavity or screw-type PD pumps.

The sugar solution is inoculated and fermented in the same tank used for saccharification. Generally, the oxygen level during fermentation should be controlled, e.g., by monitoring the oxygen level and venting the tank or aerating the mixture as necessary. It is also desirable to monitor the level of ethanol in the vessel, so that when the ethanol level begins to drop the fermentation process can be stopped, e.g., by heating or the addition of sodium bisulfite. Generally, jet mixing continues during fermentation, using the same equipment described above.

When fermentation has been completed, or completed to a desired extent, the fermentation product, e.g., an alcohol such as ethanol, is collected by distillation. Preferably, distillation is performed using a vacuum distillation unit 151, shown diagrammatically in FIG. 3. Vacuum distillation is preferred because it can be performed at substantially ambient temperatures, and thus the nutrients, enzymes and/or microorganisms present in the tank will not be damaged by distillation and can be reused. Preferrably, vacuum distillation is conducted at a pressure of less than 150 Torr, e.g., less than 125, 100, 80, 70, 60, 50, 40, or 30 Torr, or even less than 25 Torr. Generally, the pressure should be sufficiently low so as to prevent formation of an azeotrope of water and the alcohol, thus eliminating the need to later remove water from the alcohol, e.g., with 3 A molecular sieves.

Figure 3A:
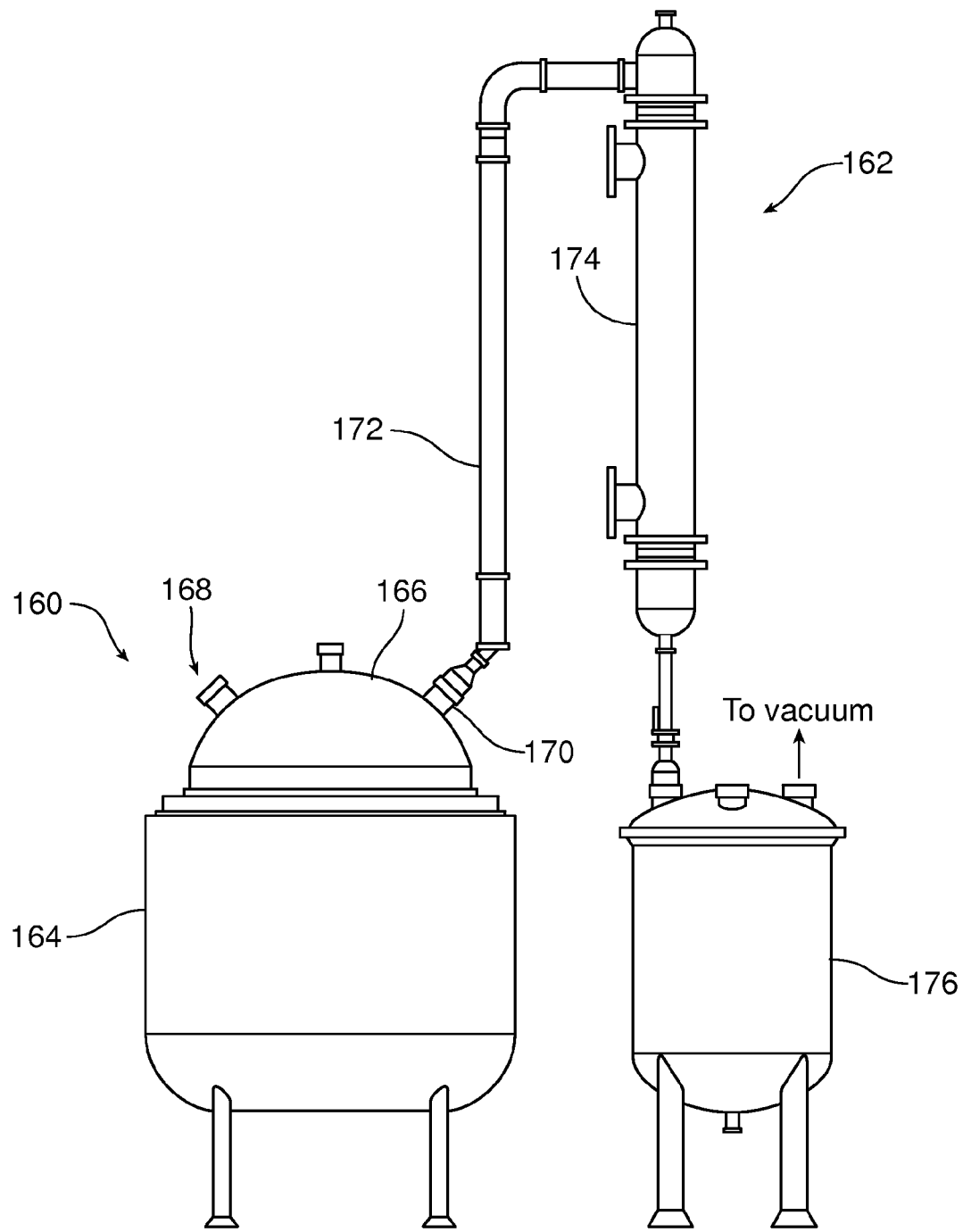
FIG. 3A is a diagrammatic side view of a tank and distillation unit suitable for use in the system of FIG. 3.

A suitable tank 160 and distillation unit 162 are shown in FIG. 3A. Tank 160 includes a jacketed vessel 164 that can be fluid cooled, e.g., with water, to maintain a desired temperature within the vessel, and a cover 166 that includes a vacuum port 168 and other ports through which materials can be delivered. The cover 166 also includes an outlet port 170, which is in fluid communication with conduit 172 of the distillation unit 162. The product of fermentation, e.g., ethanol, is drawn by the vacuum through conduit 172 to condenser 174, and collected in a covered receiving vessel 176. The system can be configured to maintain the temperature within the vessel at less than 55, 50, 45, or even less than 40° F. (less than 13, 10, 7, or 4.5° C.).

Dispersing and Mixing

Dispersing

Dispersing unit 134 may include any type of dispersing equipment that wets the feedstock with the liquid medium. Many dispersing units include a chamber and a rotor in the chamber positioned such that the feedstock and liquid medium are drawn towards the rotor axially, and forced outward radially to the periphery of the rotor and thus through the outlet of the unit, in the manner of a centrifugal pump. Depending upon the construction of the dispersing unit, a back-up pump may be required (pump 139, discussed above) to draw the fluid through the dispersing unit at high viscosities. Some dispersing units are constructed to generate very high static fluid pressure within the unit; when such units are used a back-up pump is generally not required.

Figure 4:
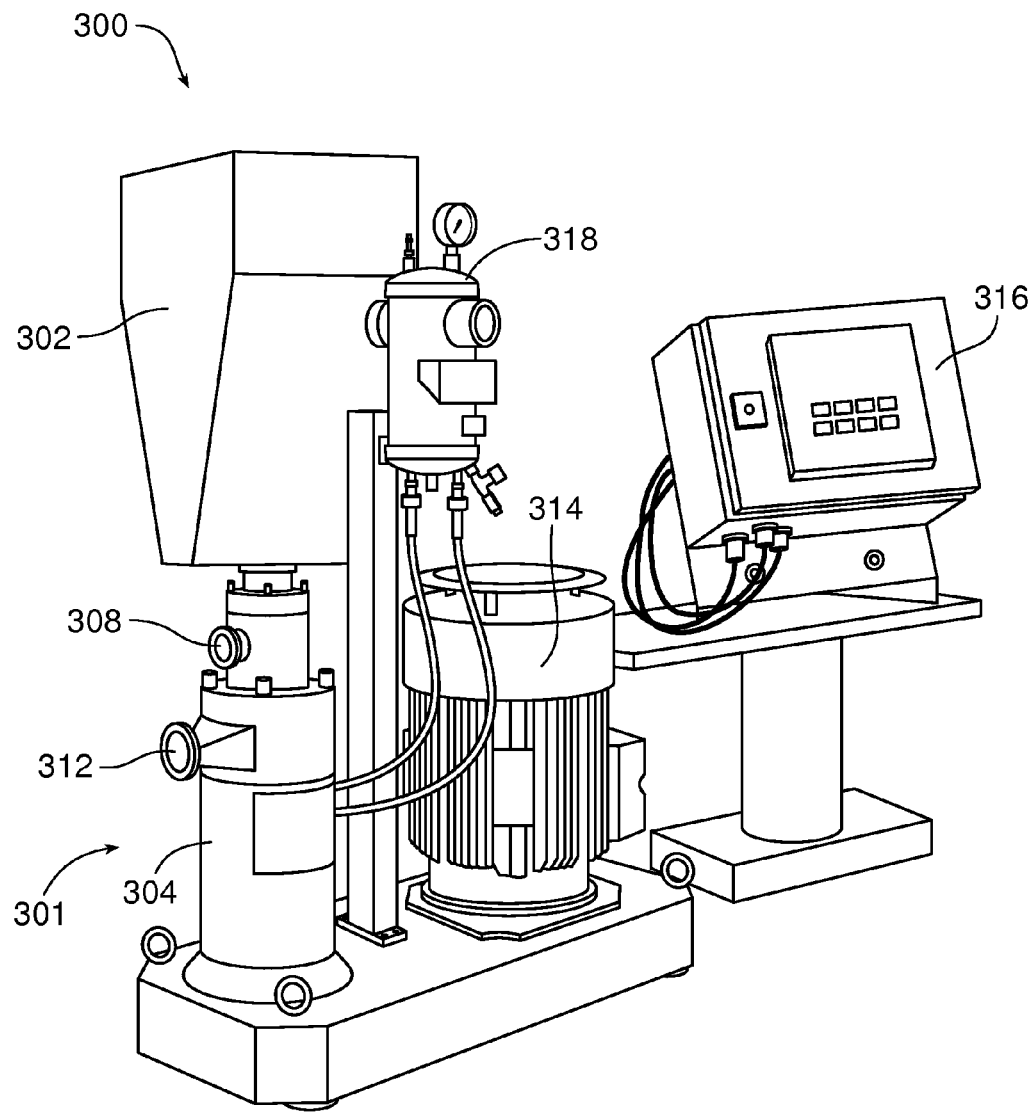
FIG. 4 is a diagrammatic perspective view of a dispersing system according to one embodiment.
Figure 5:
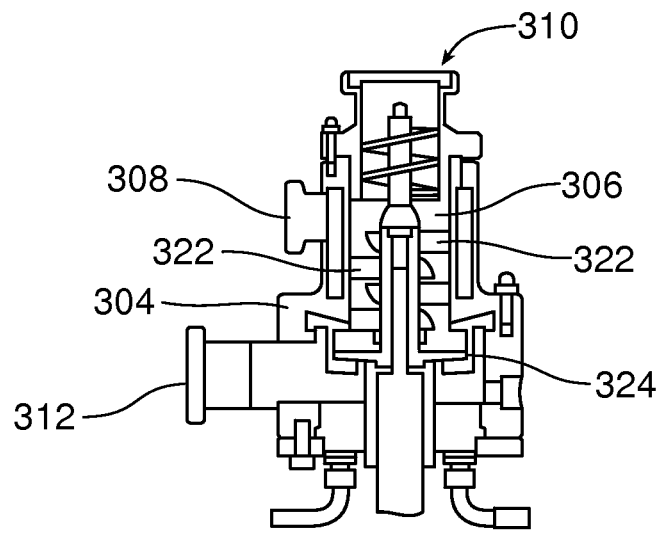
FIGS. 5 and 5A are diagrammatic cross-sectional and perspective views, respectively, of a dispersing device that can be used in the dispersing system shown in FIG. 4.
Figure 5A:
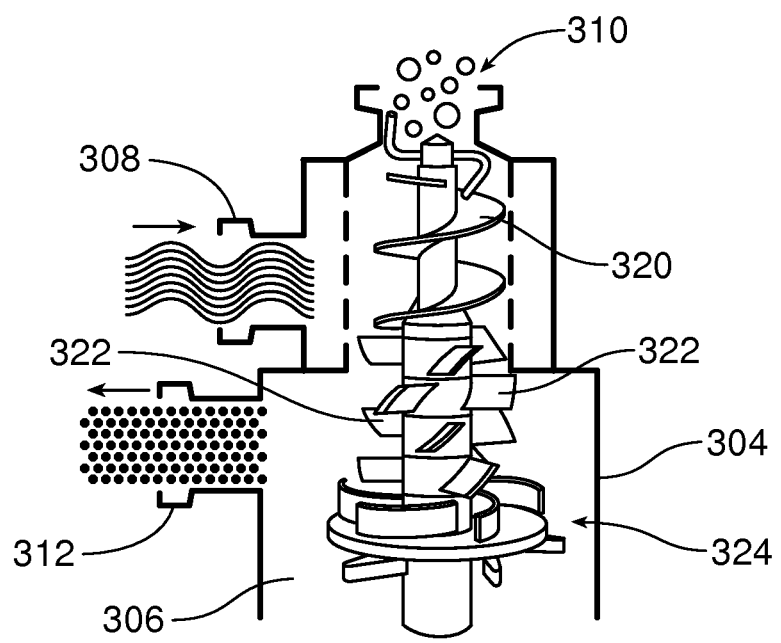

One example of a suitable dispersing system 300 is shown in FIGS. 4-5A. This system generates relatively low suction, and thus a back-up pump is typically used. Dispersing system 300 includes a receiving bin 302 which can receive feedstock from a larger hopper or bag (not shown) or other source and deliver it to dispersing unit 301. Dispersing unit 301 includes a housing 304, which defines a dispersing chamber 306 (FIG. 5A), a liquid inlet 308, a solids inlet 310 (FIG. 5A) in communication with the bin 302, and an outlet 312. The dispersing system 300 also includes a motor 314 that drives the dispersing unit 301, a user control interface 316, and a pressurized unit 318 that helps to maintain the integrity of seals within the dispersing unit 301. A valve (not shown) is disposed between the receiving bin 302 and the solids inlet 310 to meter delivery of the solids to the dispersing unit 301.

The internal structure of the dispensing unit 301 is shown in FIGS. 5-5A. After passing through solids inlet 310, the solids are moved downward by an auger 320 as the solids are contacted by the liquid entering through liquid inlet 308. The liquid and solids are then mixed by a series of mixing paddles 322, and finally by a rotor 324 (shown in detail in FIG. 5A) which is disposed in a rotor/stator arrangement relative to the side wall of the chamber 306. This series of mixing elements wets the solids with the liquid, at increasing levels of shear, resulting in a substantially homogeneous dispersion exiting through the outlet 312. The impeller, by the Venturi principle, creates a large pressure differential between the chamber 306 and the bin 302, which draws a vacuum and thus helps to draw the material from the bin into the chamber.

Figure 6:
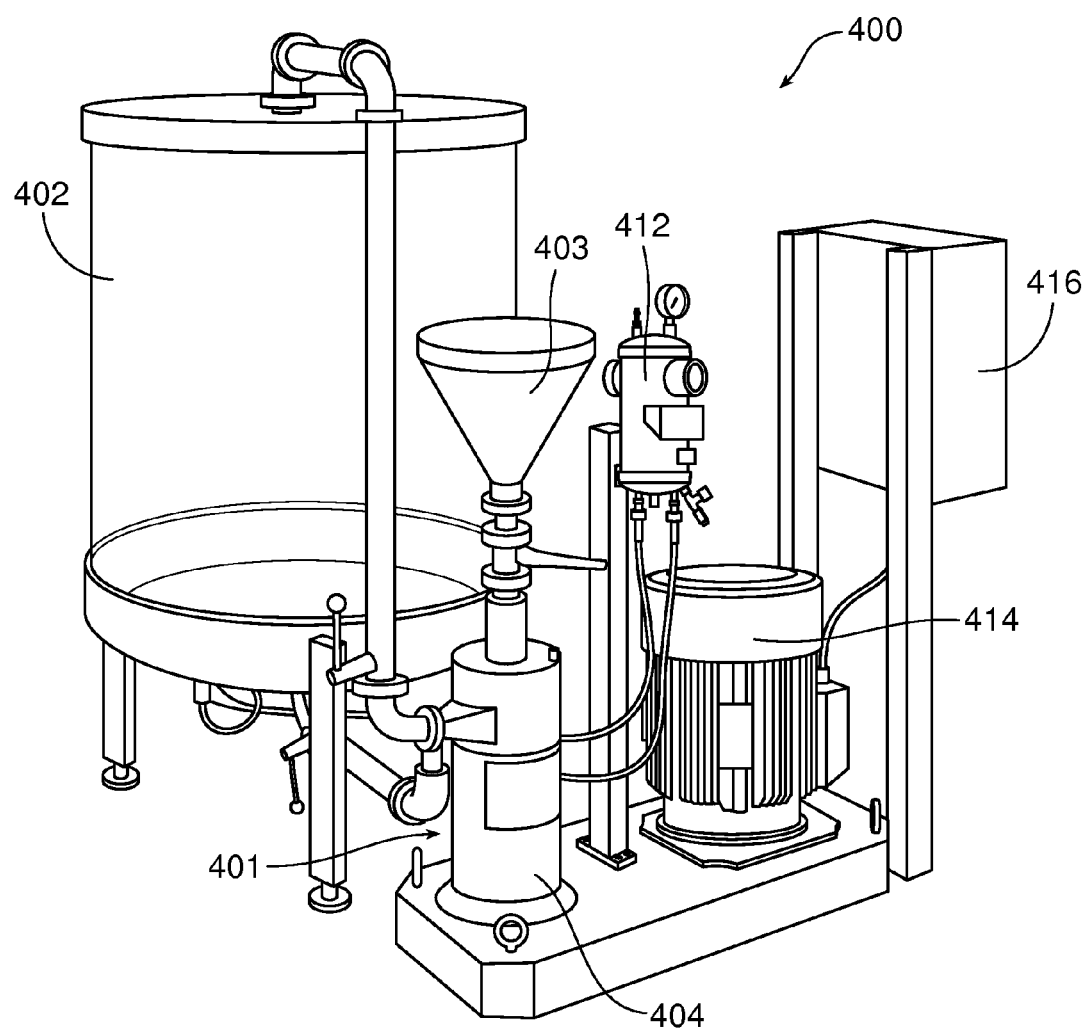
FIG. 6 is a diagrammatic perspective view of a dispersing system according to another embodiment.
Figure 7:
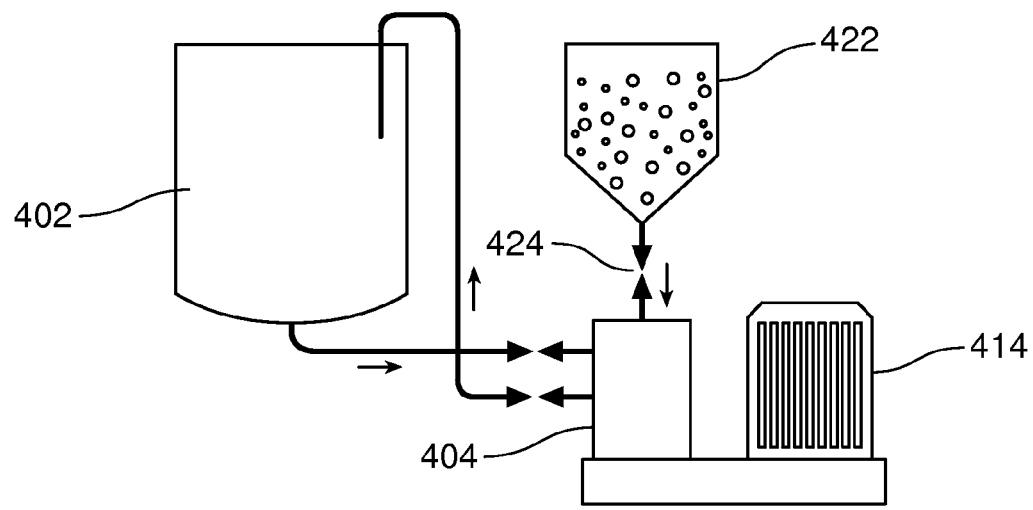
FIGS. 7 and 7A are diagrams illustrating alternative operating modes for the dispersing system shown in FIG. 6.
Figure 8:
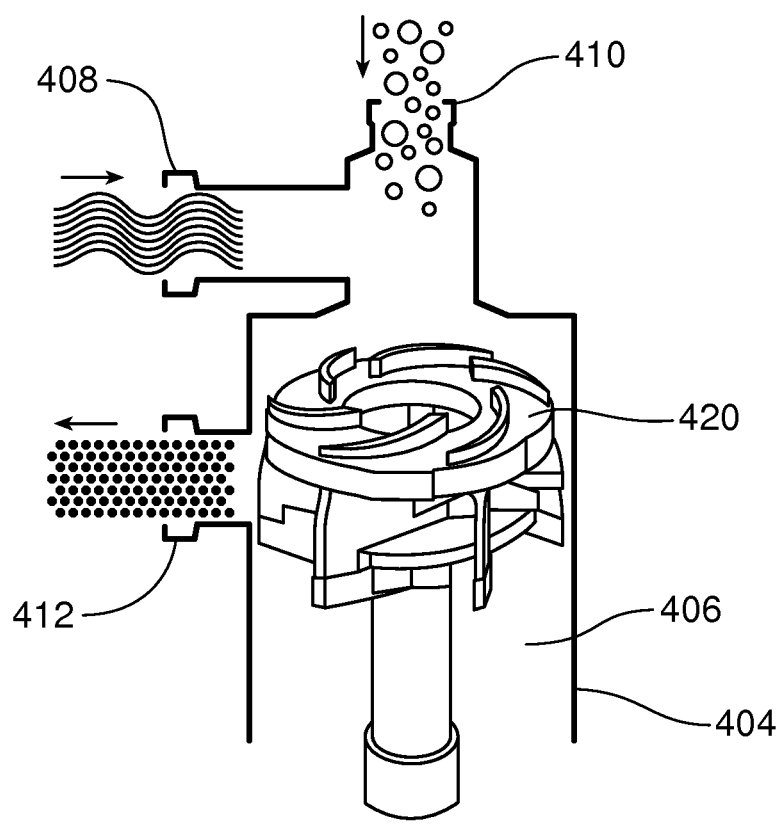
FIG. 8 is a diagrammatic perspective view of a dispersing element that can be used in the dispersing system shown in FIG. 6.

Another suitable dispersing system 400 is shown in FIGS. 6-8. This system is commercially available from IKA® Works, Wilmington, N.C., under the tradename CMS 2000. Dispersing system 400, as supplied, includes a liquids tank 402. However, if desired the relatively small tank 402 can be omitted and the remainder of the system piped into a larger tank, e.g., an industrial volume tank (not shown). System 400 also includes a solids receiving funnel 403, a dispensing unit 401 including a housing 404 having a structure similar to that of housing 304 discussed above, a motor 414, a user control interface 416, and a pressurized unit 418.

The primary difference between the dispersing system 400 and the dispersing system 300 lies in the internal structure of the dispensing units 401 and 301. The dispensing unit 401, shown in detail in FIG. 8, includes a rotor 420 which functions as an impeller and generates very high static fluid pressure within the unit. As a result, the dispersing unit functions in the manner of a centrifugal pump, and a back-up pump is generally not necessary, even at relatively high viscosities.

The rotor 420 draws the liquid from the tank into chamber 406 through inlet 408 at high suction. The liquid and the solids (entering through inlet 410) are drawn axially into the rotor 420 at high pressure, and exit the rotor 420 radially with high velocity turbulent flow that disperses the feedstock into the liquid. A substantially homogeneous dispersion exits the chamber via outlet 412 and is delivered to the tank for saccharification.

Figure 7A:
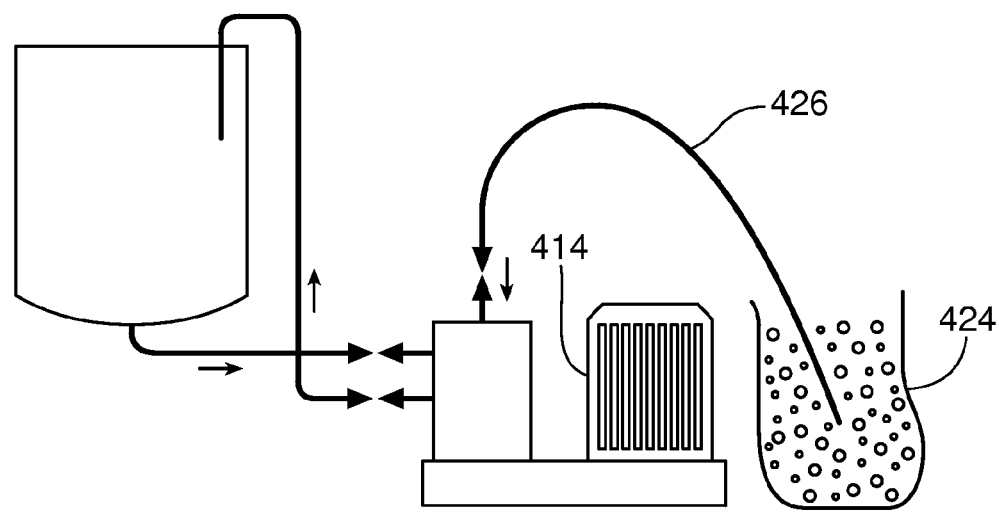

The dispersing system 400 may be operated in various modes, examples of which are shown in FIGS. 7 and 7A. In FIG. 7, the dispersing unit 401 is fed by loading the feedstock into a hopper 422 that is mounted on the solids inlet of housing 404. A valve 424 controls delivery of the feedstock to the dispersing unit 401. The feedstock can be loaded using any desired delivery technique, e.g., manually, by conveyor, pneumatic loader, or the like. In FIG. 7A, the feedstock is suctioned out of a bag or bin 424 using a suction wand 426. In this case delivery of the feedstock can be controlled by controlling the rate of suctioning. Other arrangements may be used.

The feedstock may be delivered to the dispersing unit continuously or intermittently, and the dispersing system may be run in a recirculating or "once through" mode. If desired, the dispersing unit can be used for mixing during saccharification, after initial dispersion has been completed.

Jet Mixing

Once the feedstock has been substantially dispersed in the liquid, it may be desirable to turn off the dispersing system and use a mixer that requires less energy for further mixing. Particularly advantageous mixers for this purpose are known as "jet mixers." In general, suitable mixers have in common that they produce high velocity circulating flow, for example flow in a toroidal or elliptical pattern. Generally, preferred mixers exhibit a high bulk flow rate. Preferred mixers provide this mixing action with relatively low energy consumption. It is also generally preferred that the mixer produce relatively low shear and avoid heating of the liquid medium, as shear and/or heat can deleteriously affect the saccharifying agent (or microorganism, e.g., in the case of fermentation). As will be discussed in detail below, some preferred mixers draw the mixture through an inlet into a mixing element, which may include a rotor or impeller, and then expel the mixture from the mixing element through an outlet nozzle. This circulating action, and the high velocity of the jet exiting the nozzle, assist in dispersing material that is floating on the surface of the liquid or material that has settled to the bottom of the tank, depending on the orientation of the mixing element. Mixing elements can be positioned in different orientations to disperse both floating and settling material, and the orientation of the mixing elements can in some cases be adjustable.

For example, in some preferred mixing systems the velocity $v_o$ of the jet as meets the ambient fluid is from about 2 to 300 m/s, e.g., about 5 to 150 m/s or about 10 to 100 m/s. The power consumption of the mixing system may be about 20 to 1000 KW, e.g., 30 to 570 KW or 50 to 500 KW for a 100,000 L tank.

Figure 11:
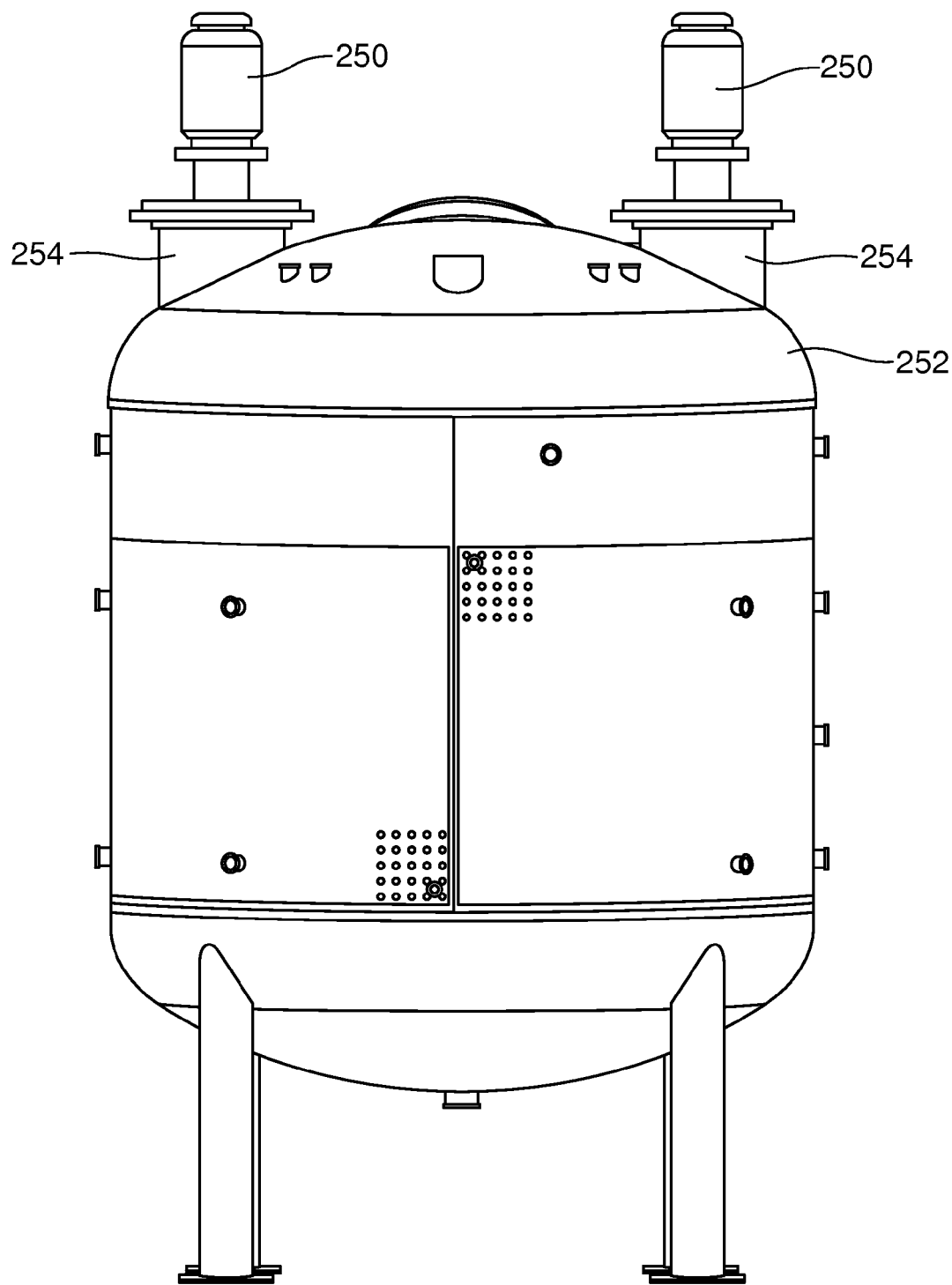
FIGS. 11 and 11A are side and cross-sectional views, respectively, of a tank having two jet mixers extending into the tank from above.
Figure 11A:
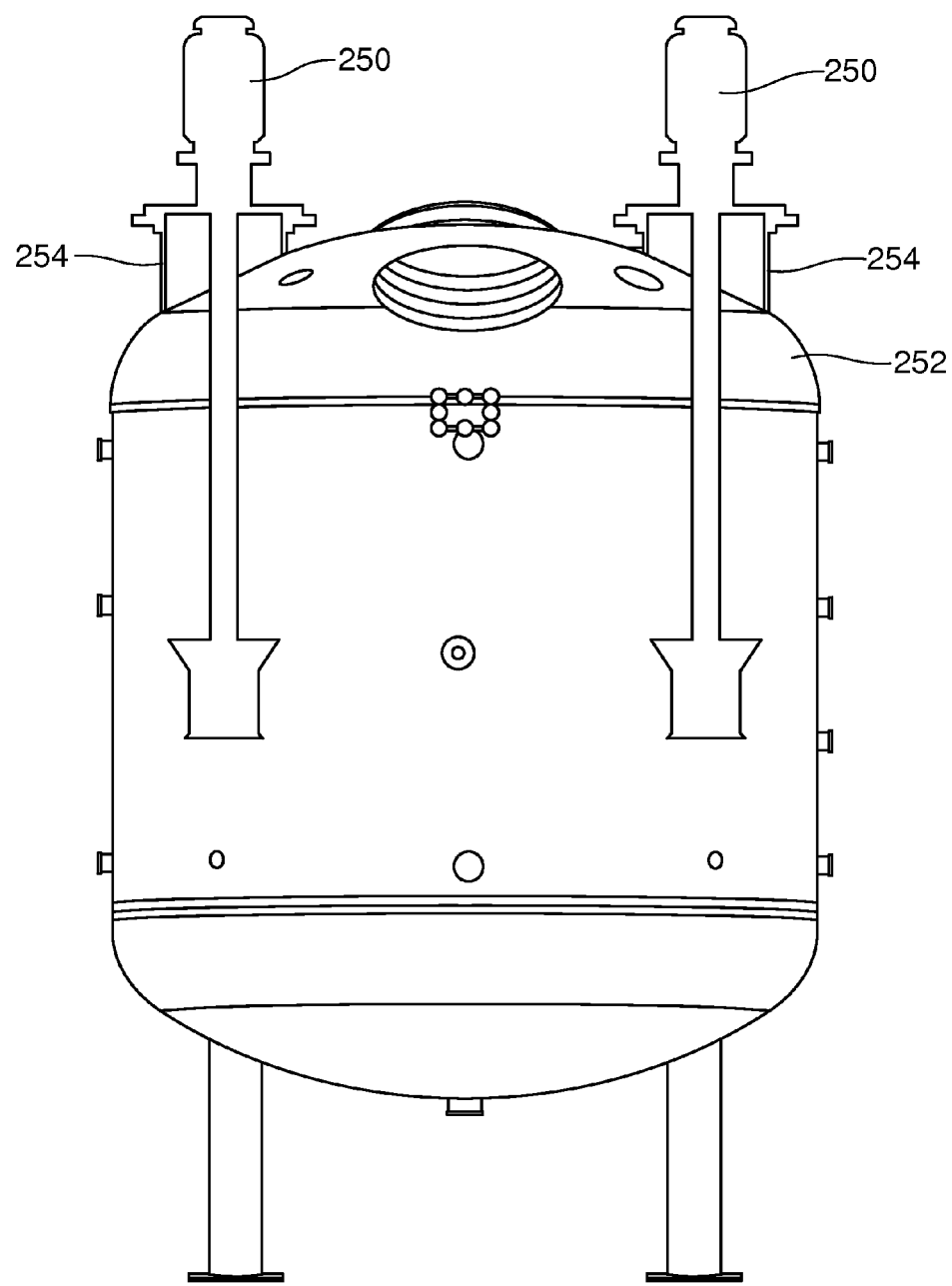

Jet mixing involves the discharge of a submerged jet, or a number of submerged jets, of high velocity liquid into a fluid medium, in this case the mixture of biomass feedstock, liquid medium and saccharifying agent. The jet of liquid penetrates the fluid medium, with its energy being dissipated by turbulence and some initial heat. This turbulence is associated with velocity gradients (fluid shear). The surrounding fluid is accelerated and entrained into the jet flow, with this secondary entrained flow increasing as the distance from the jet nozzle increases. The momentum of the secondary flow remains generally constant as the jet expands, as long as the flow does not hit a wall, floor or other obstacle. The longer the flow continues before it hits any obstacle, the more liquid is entrained into the secondary flow, increasing the bulk flow in the tank or vessel. When it encounters an obstacle, the secondary flow will lose momentum, more or less depending on the geometry of the tank, e.g., the angle at which the flow impinges on the obstacle. It is generally desirable to orient the jets and/or design the tank so that hydraulic losses to the tank walls are minimized. For example, it may be desirable for the tank to have an arcuate bottom (e.g., a domed headplate), and for the jet mixers to be oriented relatively close to the sidewalls, as shown in FIG. 11A. The tank bottom (lower head plate) may have any desired domed configuration, or may have an elliptical or conical geometry.

Jet mixing differs from most types of liquid/liquid and liquid/solid mixing in that the driving force is hydraulic rather than mechanical. Instead of shearing fluid and propelling it around the mixing vessel, as a mechanical agitator does, a jet mixer forces fluid through one or more nozzles within the tank, creating high-velocity jets that entrain other fluid. The result is shear (fluid against fluid) and circulation, which mix the tank contents efficiently.

Figure 9:
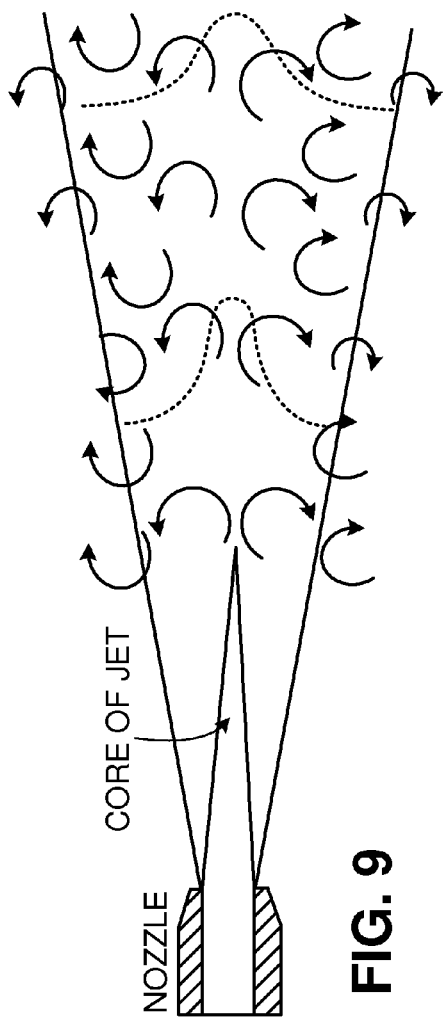
FIGS. 9 and 9A are diagrams illustrating jet flow exiting a nozzle.
Figure 9A:
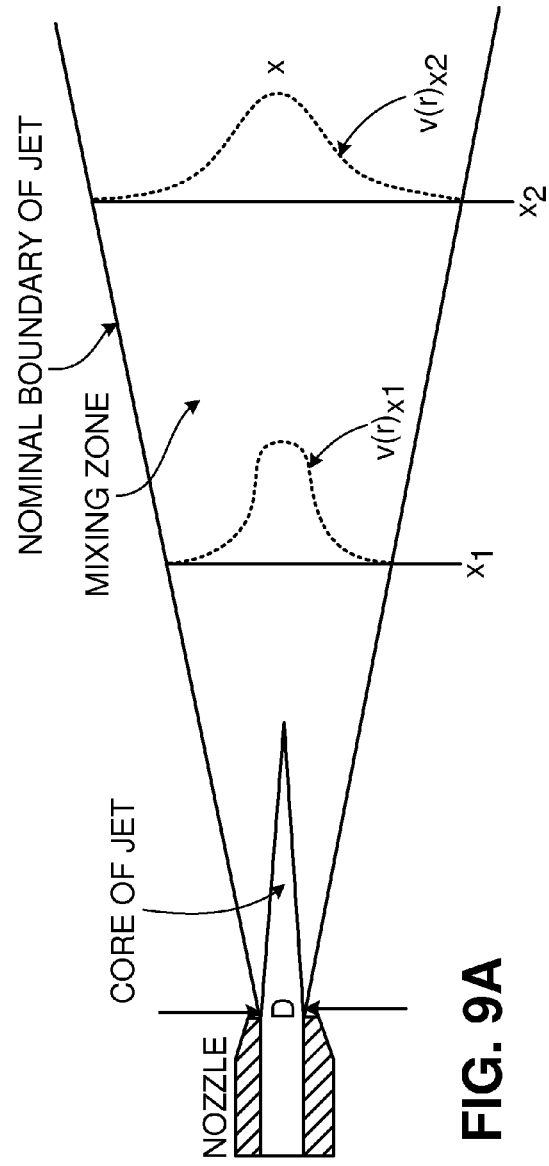

Referring to FIG. 9, the high velocity gradient between the core flow from a submerged jet and the surrounding fluid causes eddies. FIG. 9A illustrates the general characteristics of a submerged jet. As the submerged jet expands into the surrounding ambient environment the velocity profile flattens as the distance (x) from the nozzle increases. Also, the velocity gradient dv/dr changes with r (the distance from the centerline of the jet) at a given distance x, such that eddies are created which define the mixing zone (the conical expansion from the nozzle).

In an experimental study of a submerged jet in air (the results of which are applicable to any fluid, including water), Albertson et al. ("Diffusion of Submerged Jets," Paper 2409, Amer. Soc. of Civil Engineers Transactions, Vol. 115:639-697, 1950, at p. 657) developed dimensionless relationships for $v(x)_{r=0}/v_o$ (centerline velocity), $v(r)_x/v(x)_{r=0}$ (velocity profile at a given x), $Q_x/Q_o$ (flow entrainment), and $E_x/E_o$ (energy change with x):

(1) Centerline velocity, $v(x)_{r=0}/v_o$:

$$\frac{v(r=0)}{v_o} \frac{x}{D_o} = 6.2$$

(2) velocity profile at any x, $v(r)_x/v(x)_{r=0}$:

$$\log\left[\frac{v(r)_x}{v_o} \frac{x}{D}\right] = 0.79 - 33\frac{r^2}{x^2}$$

(3) Flow and energy at any x:

$$\frac{Q_x}{Q_o} = 0.32\frac{x}{D_o} \quad (10.21)$$

$$\frac{E_x}{E_o} = 4.1\frac{D_o}{x} \quad (10.22)$$

where:
v(r=0)=centerline velocity of submerged jet (m/s),
$v_o$=velocity of jet as it emerges from the nozzle (m/s),
x=distance from nozzle (m),
r=distance from centerline of jet (m),
$D_o$=diameter of nozzle (m),
$Q_x$=flow of fluid across any given plane at distance x from the nozzle (me/s),
$Q_o$=flow of fluid emerging from the nozzle (m3/s),
E=energy flux of fluid across any given plane at distance x from the nozzle (m³/s),
$E_o$=energy flux of fluid emerging from the nozzle (m³/s).

("Water Treatment Unit Processes: Physical and Chemical," David W. Hendricks, CRC Press 2006, p. 411.)

Jet mixing is particularly cost-effective in large-volume (over 1,000 gal) and low-viscosity (under 1,000 cPs) applications. It is also generally advantageous that in most cases the pump or motor of the jet mixer not be submerged, e.g., when a pump is used it is generally located outside the vessel.

One advantage of jet mixing is that the temperature of the ambient fluid (other than directly adjacent the exit of the nozzle, where there may be some localized heating) is increased only slightly if at all. For example, the temperature may be increased by less than 5° C., less than 1° C., or not to any measurable extent.

Jet-Flow Agitators

Figure 10:
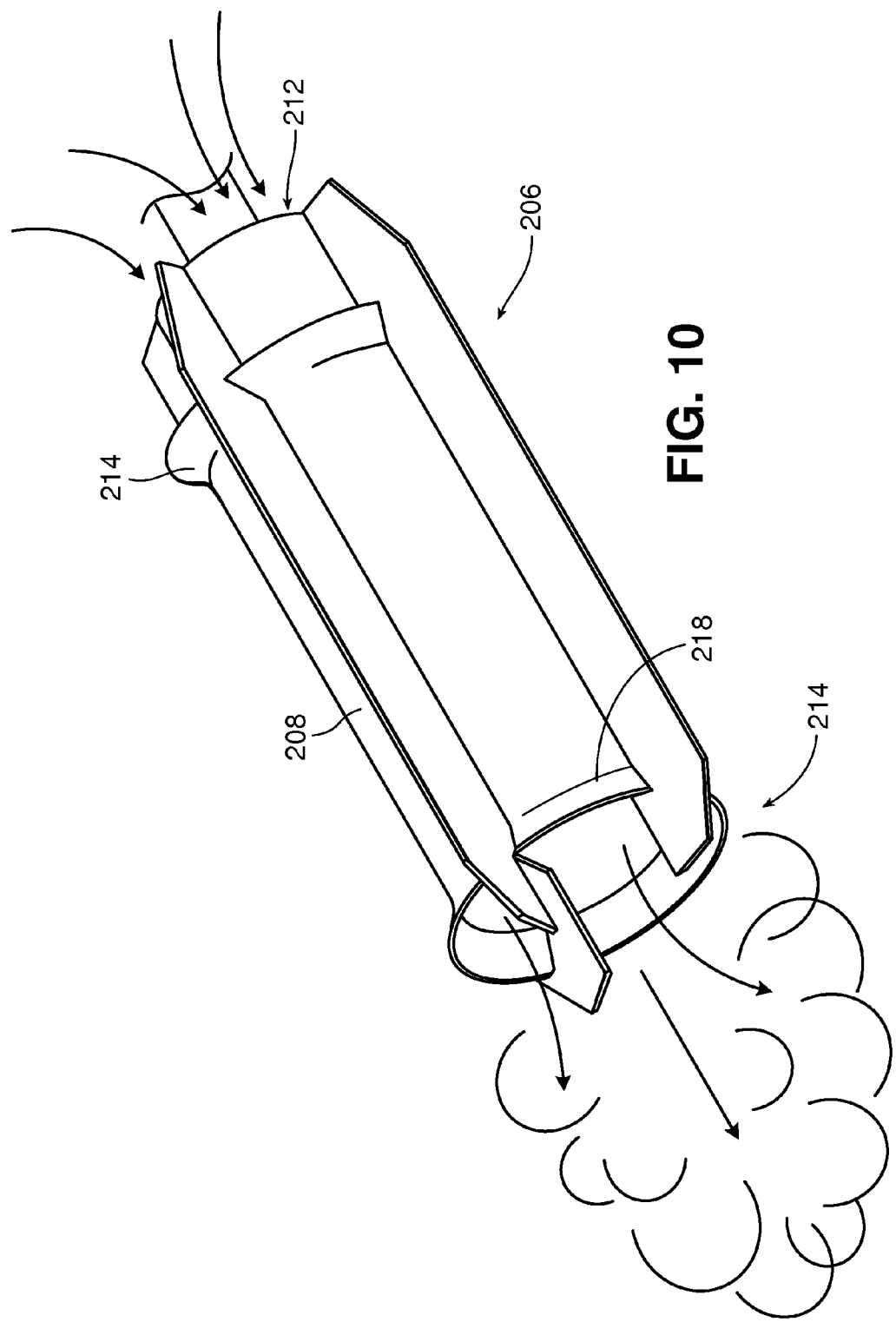
FIG. 10 is a diagrammatic perspective view of a jet-flow agitator according to one embodiment.
Figure 10A:
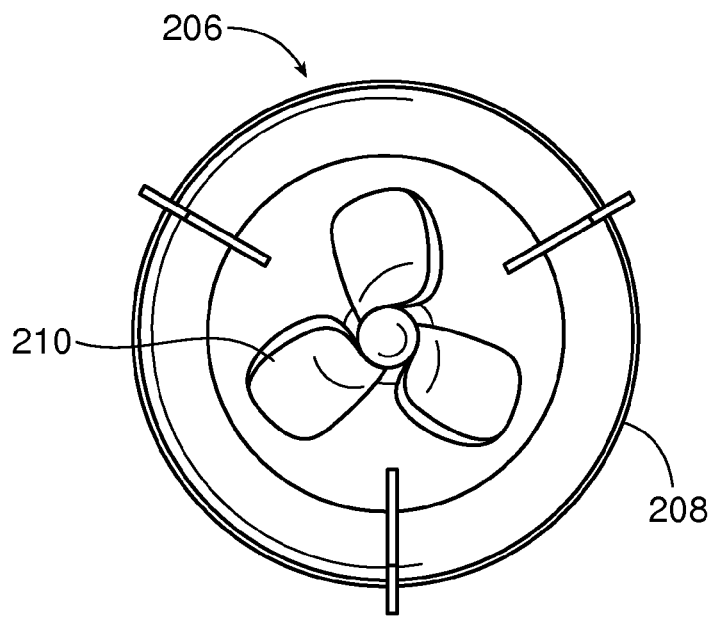
FIG. 10A is an enlarged perspective view of the impeller and jet tube of the jet-flow agitator of FIG. 10.

One type of jet-flow agitator is shown in FIGS. 10-10A. This type of mixer is available commercially, e.g., from IKA under the tradename ROTOTRON™. Referring to FIG. 10, the mixer 200 includes a motor 202, which rotates a drive shaft 204. A mixing element 206 is mounted at the end of the drive shaft 204. As shown in FIG. 10A, the mixing element 206 includes a shroud 208 and, within the shroud, an impeller 210. As indicated by the arrows, when the impeller is rotated in its "forward" direction, the impeller 210 draws liquid in through the open upper end 212 of the shroud and forces the liquid out through the open lower end 214. Liquid exiting end 214 is in the form of a high velocity stream or jet. If the direction of rotation of the impeller 210 is reversed, liquid can be drawn in through the lower end 214 and ejected through the upper end 212. This can be used, for example, to suck in solids that are floating near or on the surface of the liquid in a tank or vessel. (It is noted that "upper" and "lower" refer to the orientation of the mixer in FIG. 10; the mixer may be oriented in a tank so that the upper end is below the lower end.)

The shroud 208 includes flared areas 216 and 218 adjacent its ends. These flared areas are believed to contribute to the generally toroidal flow that is observed with this type of mixer. The geometry of the shroud and impeller also concentrate the flow into a high velocity stream using relatively low power consumption.

Preferably, the clearance between the shroud 208 and the impeller 210 is sufficient so as to avoid excessive milling of the material as it passes through the shroud. For example, the clearance may be at least 10 times the average particle size of the solids in the mixture, preferably at least 100 times.

In some implementations, the shaft 204 is configured to allow gas delivery through the shaft. For example, the shaft 204 may include a bore (not shown) through which gas is delivered, and one or more orifices through which gas exits into the mixture. The orifices may be within the shroud 208, to enhance mixing, and/or at other locations along the length of the shaft 204.

Figure 10B:
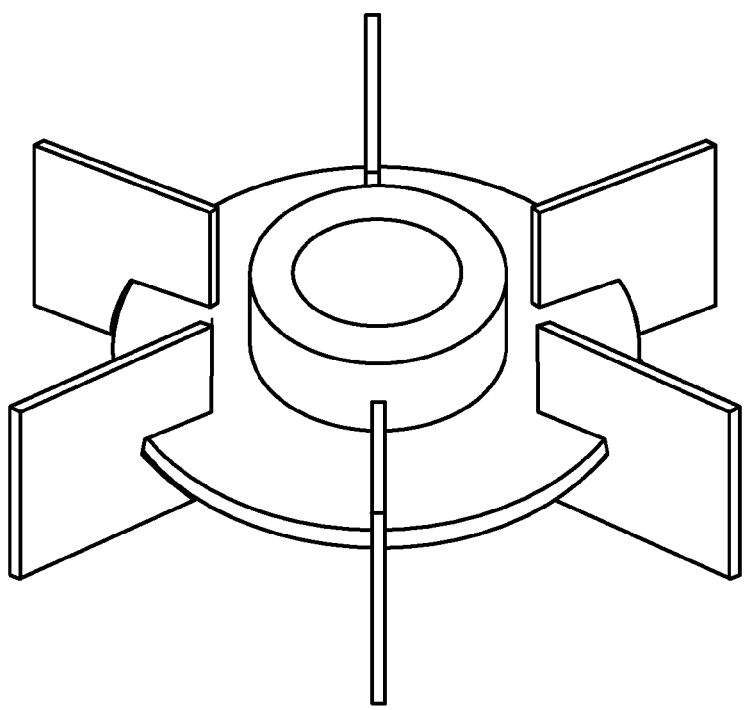
FIG. 10B is an enlarged perspective view of an alternate impeller.

The impeller 210 may have any desired geometry that will draw liquid through the shroud at a high velocity. The impeller is preferably a marine impeller, as shown in FIG. 10A, but may have a different design, for example, a Rushton impeller as shown in FIG. 10B, or a modified Rushton impeller, e.g., tilted so as to provide some axial flow.

In order to generate the high velocity flow through the shroud, the motor 202 is preferably a high speed, high torque motor, e.g., capable of operating at 500 to 20,000 RPM, e.g., 3,000 to 10,000 RPM. However, the larger the mixer (e.g., the larger the shroud and/or the larger the motor) the lower the rotational speed can be. Thus, if a large mixer is used, such as a 5 hp, 10 hp, 20 hp, or 30 hp or greater, the motor may be designed to operate at lower rotational speeds, e.g., less than 2000 RPM, less than 1500 RPM, or even 500 RPM or less. For example, a mixer sized to mix a 10,000-20,000 liter tank may operate at speeds of 900 to 1,200 RPM. The torque of the motor is preferably self-adjusting, to maintain a relatively constant impeller speed as the mixing conditions change over time, e.g., due to saccharification of the solids.

Advantageously, the mixer can be oriented at any desired angle or location in the tank, to direct the jet flow in a desired direction. FIGS. 11 and 11A illustrate one embodiment, in which two jet mixers extend downwardly into a tank 252 through ports 254.

Moreover, as discussed above, depending on the direction of rotation of the impeller the mixer can be used to draw fluid from either end of the shroud.

In some implementations, two or more jet mixers are positioned in the vessel, with one or more being configured to jet fluid upward ("up pump") and one or more being configured to jet fluid downward ("down pump"). In some cases, an up pumping mixer will be positioned adjacent a down pumping mixer, to enhance the turbulent flow created by the mixers. If desired, one or more mixers may be switched between upward flow and downward flow during processing. It may be advantageous to switch all or most of the mixers to up pumping mode during initial dispersion of the feedstock in the liquid medium, particularly if the feedstock is dumped or blown onto the surface of the liquid, as up pumping creates significant turbulence at the surface. Up pumping can also be used during fermentation to help remove $CO_2$ from the liquid by causing the gas to bubble to the surface where it can be vented.

Other suitable jet mixers are described in U.S. Provisional Application No. 61/218,832, filed Jun. 19, 2009, and U.S. Ser. No. 12/782,694, filed May 24, 2010, the full disclosures of which are incorporated herein by reference.

Materials

Biomass Materials

The biomass can be, e.g., a cellulosic or lignocellulosic material. Such materials include paper and paper products (e.g., polycoated paper and Kraft paper), wood, wood-related materials, e.g., particle board, grasses, rice hulls, bagasse, jute, hemp, flax, bamboo, sisal, abaca, straw, switchgrass, alfalfa, hay, corn cobs, corn stover, coconut hair; and materials high in α-cellulose content, e.g., cotton. Feedstocks can be obtained from virgin scrap textile materials, e.g., remnants, post consumer waste, e.g., rags. When paper products are used they can be virgin materials, e.g., scrap virgin materials, or they can be post-consumer waste. Aside from virgin raw materials, post-consumer, industrial (e.g., offal), and processing waste (e.g., effluent from paper processing) can also be used as fiber sources. Biomass feedstocks can also be obtained or derived from human (e.g., sewage), animal or plant wastes. Additional cellulosic and lignocellulosic materials have been described in U.S. Pat. Nos. 6,448,307, 6,258,876, 6,207,729, 5,973,035 and 5,952,105.

In some embodiments, the biomass material includes a carbohydrate that is or includes a material having one or more β-1,4-linkages and having a number average molecular weight between about 3,000 and 50,000. Such a carbohydrate is or includes cellulose (I), which is derived from (β-glucose 1) through condensation of β(1,4)-glycosidic bonds. This linkage contrasts itself with that for α(1,4)-glycosidic bonds present in starch and other carbohydrates.

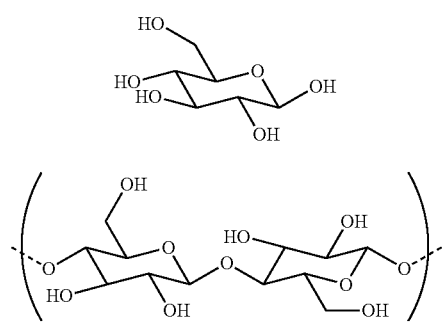

I

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials.

In some cases the biomass is a microbial material. Microbial sources include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture systems.

Saccharifying Agents

Suitable enzymes include cellobiases and cellulases capable of degrading biomass.

Suitable cellobiases include a cellobiase from *Aspergillus niger* sold under the tradename NOVOZYME 188™.

Cellulases are capable of degrading biomass, and may be of fungal or bacterial origin. Suitable enzymes include cellulases from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cephalosporium, Scytalidium, Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum*, and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei*, and *Trichoderma koningii*), alkalophilic *Bacillus* (see, for example, U.S. Pat. No. 3,844,890 and EP 458162), and *Streptomyces* (see, e.g., EP 458162) may be used.

Enzyme complexes may be utilized, such as those available from Genencore under the tradename ACCELLERASE®, for example, Accellerase® 1500 enzyme complex.

Accellerase® 1500 enzyme complex contains multiple enzyme activities, mainly exoglucanase, endoglucanase (2200-2800 CMC U/g), hemi-cellulase, and beta-glucosidase (525-775 pNPG U/g), and has a pH of 4.6 to 5.0. The endoglucanase activity of the enzyme complex is expressed in carboxymethylcellulose activity units (CMC U), while the beta-glucosidase activity is reported in pNP-glucoside activity units (pNPG U). In one embodiment, a blend of Accellerase® 1500 enzyme complex and NOVOZYME™ 188 cellobiase is used.

In some implementations, the saccharifying agent comprises an acid, e.g., a mineral acid. When an acid is used, co-products may be generated that are toxic to microorganisms, in which case the process can further include removing such co-products. Removal may be performed using an activated carbon, e.g., activated charcoal, or other suitable techniques.

Fermentation Agents

The microorganism(s) used in fermentation can be natural microorganisms and/or engineered microorganisms. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized.

Suitable fermenting microorganisms have the ability to convert carbohydrates, such as glucose, xylose, arabinose, mannose, galactose, oligosaccharides or polysaccharides into fermentation products. Fermenting microorganisms include strains of the genus *Sacchromyces* spp. e.g., *Sacchromyces cerevisiae* (baker's yeast), *Saccharomyces distaticus, Saccharomyces uvarum*; the genus *Kluyveromyces*, e.g., species *Kluyveromyces marxianus, Kluyveromyces fragilis*; the genus *Candida*, e.g., *Candida pseudotropicalis*, and *Candida brassicae, Pichia stipitis* (a relative of *Candida shehatae*, the genus *Clavispora*, e.g., species *Clavispora lusitaniae* and *Clavispora opuntiae*, the genus *Pachysolen*, e.g., species *Pachysolen tannophilus*, the genus *Bretannomyces*, e.g., species *Bretannomyces clausenii* (Philippidis, G. P., 1996, Cellulose bioconversion technology, in Handbook on Bioethanol: Production and Utilization, Wyman, C. E., ed., Taylor & Francis, Washington, D.C., 179-212).

Commercially available yeasts include, for example, Red Star®/Lesaffre Ethanol Red (available from Red Star/Lesaffre, USA), FALI® (available from Fleischmann's Yeast, a division of Burns Philip Food Inc., USA), SUPERSTART® (available from Alltech, now Lalemand), GERT STRAND® (available from Gert Strand AB, Sweden) and FERMOL® (available from DSM Specialties).

Bacteria may also be used in fermentation, e.g., *Zymomonas mobilis* and *Clostridium thermocellum* (Philippidis, 1996, supra).

Additives

Antibiotics

While it is generally preferred to have a high sugar concentration in the saccharified solution, lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high.

Surfactants

The addition of surfactants can enhance the rate of saccharification. Examples of surfactants include non-ionic surfactants, such as a Tween® 20 or Tween® 80 polyethylene glycol surfactants, ionic surfactants, or amphoteric surfactants. Other suitable surfactants include octylphenol ethoxylates such as the TRITON™ X series nonionic surfactants commercially available from Dow Chemical. A surfactant can also be added to keep the sugar that is being produced in solution, particularly in high concentration solutions.

Saccharification Medium

In one embodiment, the medium has the following concentrations of components:

| | |
|---|---|
| Yeast nitrogen base | 1.7 g/L |
| Urea | 2.27 g/L |
| Peptone | 6.56 g/L |
| Tween ® 80 surfactant | 10 g/L |

Physical Treatment of Feedstock

Physical Preparation

In some cases, methods can include a physical preparation, e.g., size reduction of materials, such as by cutting, grinding, shearing, pulverizing or chopping. For example, in some cases, loose feedstock (e.g., recycled paper, starchy materials, coal or switchgrass) is prepared by shearing or shredding. For example, in other cases, material is first pretreated or processed using one or more any of the methods described herein, such as radiation, sonication, oxidation, pyrolysis or steam explosion, and then size reduced or further size reduced. Treating first and then size reducing can be advantageous since treated materials tend to be more brittle and, therefore, easier to size reduce. Screens and/or magnets can be used to remove oversized or undesirable objects such as, for example, rocks or nails from the feed stream.

Feed preparation systems can be configured to produce streams with specific characteristics such as, for example, specific maximum sizes, specific length-to-width, or specific surface areas ratios. Physical preparation can increase the rate of reactions or reduce the processing time required by opening up the materials and making them more accessible to processes and/or reagents, such as reagents in a solution. The bulk density of feedstocks can be controlled (e.g., increased). In some situations, it can be desirable to prepare a low bulk density material, densify the material (e.g., to make it easier and less costly to transport to another site), and then revert the material to a lower bulk density state.

Size Reduction

In some embodiments, the material to be processed is in the form of a fibrous material that includes fibers provided by shearing a fiber source. For example, the shearing can be performed with a rotary knife cutter.

For example, a fiber source, e.g., that is recalcitrant or that has had its recalcitrance level reduced, can be sheared, e.g., in a rotary knife cutter, to provide a first fibrous material. The first fibrous material is passed through a first screen, e.g., having an average opening size of 1.59 mm or less (1/16 inch, 0.0625 inch), provide a second fibrous material. If desired, the fiber source can be cut prior to the shearing, e.g., with a shredder. For example, when a paper is used as the fiber source, the paper can be first cut into strips that are, e.g., ¼- to ½-inch wide, using a shredder, e.g., a counterrotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of the fiber source and the passing of the resulting first fibrous material through a first screen are performed concurrently. The shearing and the passing can also be performed in a batch-type process.

For example, a rotary knife cutter can be used to concurrently shear the fiber source and screen the first fibrous material. A rotary knife cutter includes a hopper that can be loaded with a shredded fiber source prepared by shredding a fiber source. The shredded fiber source In some implementations, the feedstock is physically treated prior to saccharification and/or fermentation. Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment method is used, the methods can be applied at the same time or at different times. Other processes that change a molecular structure of a biomass feedstock may also be used, alone or in combination with the processes disclosed herein.

Mechanical Treatments

In some cases, methods can include mechanically treating the biomass feedstock. Mechanical treatments include, for example, cutting, milling, pressing, grinding, shearing and chopping. Milling may include, for example, ball milling, hammer milling, rotor/stator dry or wet milling, or other types of milling. Other mechanical treatments include, e.g., stone grinding, cracking, mechanical ripping or tearing, pin grinding or air attrition milling.

Mechanical treatment can be advantageous for "opening up," "stressing," breaking and shattering the cellulosic or lignocellulosic materials, making the cellulose of the materials more susceptible to chain scission and/or reduction of crystallinity. The open materials can also be more susceptible to oxidation when irradiated.

In some cases, the mechanical treatment may include an initial preparation of the feedstock as received, e.g., size reduction of materials, such as by cutting, grinding, shearing, pulverizing or chopping. For example, in some cases, loose feedstock (e.g., recycled paper, starchy materials, or switchgrass) is prepared by shearing or shredding.

Alternatively, or in addition, the feedstock material can first be physically treated by one or more of the other physical treatment methods, e.g., chemical treatment, radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the molecular structure of the material by mechanical treatment.

In some embodiments, the feedstock material is in the form of a fibrous material, and mechanical treatment includes shearing to expose fibers of the fibrous material. Shearing can be performed, for example, using a rotary knife cutter. Other methods of mechanically treating the feedstock include, for example, milling or grinding. Milling may be performed using, for example, a hammer mill, ball mill, colloid mill, conical or cone mill, disk mill, edge mill, Wiley mill or grist mill. Grinding may be performed using, for example, a stone grinder, pin grinder, coffee grinder, or burr grinder. Grinding may be provided, for example, by a reciprocating pin or other element, as is the case in a pin mill. Other mechanical treatment methods include mechanical ripping or tearing, other methods that apply pressure to the material, and air attrition milling. Suitable mechanical treatments further include any other technique that changes the molecular structure of the feedstock.

If desired, the mechanically treated material can be passed through a screen, e.g., having an average opening size of 1.59 mm or less (1/16 inch, 0.0625 inch). In some embodiments, shearing, or other mechanical treatment, and screening are performed concurrently. For example, a rotary knife cutter can be used to concurrently shear and screen the feedstock. The feedstock is sheared between stationary blades and rotating blades to provide a sheared material that passes through a screen, and is captured in a bin.

The cellulosic or lignocellulosic material can be mechanically treated in a dry state (e.g., having little or no free water on its surface), a hydrated state (e.g., having up to ten percent by weight absorbed water), or in a wet state, e.g., having between about 10 percent and about 75 percent by weight water. The fiber source can even be mechanically treated while partially or fully submerged under a liquid, such as water, ethanol or isopropanol.

The fiber sourcecellulosic or lignocellulosic material can also be mechanically treated under a gas (such as a stream or atmosphere of gas other than air), e.g., oxygen or nitrogen, or steam.

If desired, lignin can be removed from any of the fibrous materials that include lignin. Also, to aid in the breakdown of the materials that include cellulose, the material can be treated prior to or during mechanical treatment or irradiation with heat, a chemical (e.g., mineral acid, base or a strong oxidizer such as sodium hypochlorite) and/or an enzyme. For example, grinding can be performed in the presence of an acid.

Mechanical treatment systems can be configured to produce streams with specific morphology characteristics such as, for example, surface area, porosity, bulk density, and, in the case of fibrous feedstocks, fiber characteristics such as length-to-width ratio.

In some embodiments, a BET surface area of the mechanically treated material is greater than 0.1 $m^2/g$, e.g., greater than 0.25 $m^2/g$, greater than 0.5 $m^2/g$, greater than 1.0 $m^2/g$, greater than 1.5 $m^2/g$, greater than 1.75 $m^2/g$, greater than 5.0 $m^2/g$, greater than 10 $m^2/g$, greater than 25 $m^2/g$, greater than 35 $m^2/g$, greater than 50 $m^2/g$, greater than 60 $m^2/g$, greater than 75 $m^2/g$, greater than 100 $m^2/g$, greater than 150 $m^2/g$, greater than 200 $m^2/g$, or even greater than 250 $m^2/g$.

A porosity of the mechanically treated material can be, e.g., greater than 20 percent, greater than 25 percent, greater than 35 percent, greater than 50 percent, greater than 60 percent, greater than 70 percent, greater than 80 percent, greater than 85 percent, greater than 90 percent, greater than 92 percent, greater than 94 percent, greater than 95 percent, greater than 97.5 percent, greater than 99 percent, or even greater than 99.5 percent.

In some embodiments, after mechanical treatment the material has a bulk density of less than 0.25 $g/cm^3$, e.g., 0.20 $g/cm^3$, 0.15 $g/cm^3$, 0.10 $g/cm^3$, 0.05 $g/cm^3$ or less, e.g., 0.025 $g/cm^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

If the feedstock is a fibrous material the fibers of the fibrous materials mechanically treated material can have a relatively large average length-to-diameter ratio (e.g., greater than 20-to-1), even if they have been sheared more than once. In addition, the fibers of the fibrous materials described herein may have a relatively narrow length and/or length-to-diameter ratio distribution.

As used herein, average fiber widths (e.g., diameters) are those determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

If the second feedstock is a fibrous material 14 the average length-to-diameter ratio of fibers of the mechanically treated material can be, e.g. greater than 8/1, e.g., greater than 10/1, greater than 15/1, greater than 20/1, greater than 25/1, or greater than 50/1. An average fiber length of the mechanically treated material can be, e.g., between about 0.5 mm and 2.5 mm, e.g., between about 0.75 mm and 1.0 mm, and an average width (e.g., diameter) of the second fibrous material 14 can be, e.g., between about 5 µm and 50 µm, e.g., between about 10 µm and 30 µm.

In some embodiments, if the feedstock is a fibrous material, the standard deviation of the fiber length of the mechanically treated material can be less than 60 percent of an average fiber length of the mechanically treated material, e.g., less than 50 percent of the average length, less than 40 percent of the average length, less than 25 percent of the average length, less than 10 percent of the average length, less than 5 percent of the average length, or even less than 1 percent of the average length.

In some situations, it can be desirable to prepare a low bulk density material, densify the material (e.g., to make it easier and less costly to transport to another site), and then revert the material to a lower bulk density state. Densified materials can be processed by any of the methods described herein, or any material processed by any of the methods described herein can be subsequently densified, e.g., as disclosed in U.S. Ser. No. 12/429,045 and WO 2008/073186, the full disclosures of which are incorporated herein by reference.

Treatment to Solubilize, Reduce Recalcitrance or Functionalize

Materials that have or have not been physically prepared can be treated for use in any production process described herein. One or more of the production processes described below may be included in the recalcitrance reducing operating unit discussed above. Alternatively, or in addition, other processes for reducing recalcitrance may be included.

Treatment processes utilized by the recalcitrance reducing operating unit can include one or more of irradiation, sonication, oxidation, pyrolysis or steam explosion. Treatment methods can be used in combinations of two, three, four, or even all of these technologies (in any order).

Radiation Treatment

One or more radiation processing sequences can be used to process materials from the feedstock, and to provide a wide variety of different sources to extract useful substances from the feedstock, and to provide partially degraded organic structurally modified material which functions as input to further processing steps and/or sequences. Irradiation can, for example, reduce the molecular weight and/or crystallinity of feedstock. Radiation can also sterilize the materials, or any media needed to bioprocess the material.

In some embodiments, energy deposited in a material that releases an electron from its atomic orbital is used to irradiate the materials. The radiation may be provided by 1) heavy charged particles, such as alpha particles or protons, 2) electrons, produced, for example, in beta decay or electron beam accelerators, or 3) electromagnetic radiation, for example, gamma rays, x rays, or ultraviolet rays. In one approach, radiation produced by radioactive substances can be used to irradiate the feedstock. In some embodiments, any combination in any order or concurrently of (1) through (3) may be utilized. In another approach, electromagnetic radiation (e.g., produced using electron beam emitters) can be used to irradiate the feedstock. The doses applied depend on the desired effect and the particular feedstock.

In some instances when chain scission is desirable and/or polymer chain functionalization is desirable, particles heavier than electrons, such as protons, helium nuclei, argon ions, silicon ions, neon ions, carbon ions, phosphorus ions, oxygen ions or nitrogen ions can be utilized. When ring-opening chain scission is desired, positively charged particles can be utilized for their Lewis acid properties for enhanced ring-opening chain scission. For example, when maximum oxidation is desired, oxygen ions can be utilized, and when maximum nitration is desired, nitrogen ions can be utilized. The use of heavy particles and positively charged particles is described in U.S. Ser. No. 12/417,699, the full disclosure of which is incorporated herein by reference.

In one method, a first material that is or includes cellulose having a first number average molecular weight ($M_{N1}$) is irradiated, e.g., by treatment with ionizing radiation (e.g., in the form of gamma radiation, X-ray radiation, 100 nm to 280 nm ultraviolet (UV) light, a beam of electrons or other charged particles) to provide a second material that includes cellulose having a second number average molecular weight ($M_{N2}$) lower than the first number average molecular weight. The second material (or the first and second material) can be combined with a microorganism (with or without enzyme treatment) that can utilize the second and/or first material or its constituent sugars or lignin to produce an intermediate or a product, such as those described herein.

Since the second material includes cellulose having a reduced molecular weight relative to the first material, and in some instances, a reduced crystallinity as well, the second material is generally more dispersible, swellable and/or soluble, e.g., in a solution containing a microorganism and/or an enzyme. These properties make the second material easier to process and more susceptible to chemical, enzymatic and/or biological attack relative to the first material, which can greatly improve the production rate and/or production level of a desired product, e.g., ethanol. Radiation can also sterilize the materials or any media needed to bioprocess the material.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the material's susceptibility to chemical, enzymatic or biological attack. In some embodiments, to increase the level of the oxidation of the second material relative to the first material, the irradiation is performed under an oxidizing environment, e.g., under a blanket of air or oxygen, producing a second material that is more oxidized than the first material. For example, the second material can have more hydroxyl groups, aldehyde groups, ketone groups, ester groups or carboxylic acid groups, which can increase its hydrophilicity.

Ionizing Radiation

Each form of radiation ionizes the carbon-containing material via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part due to their acidic nature. When particles are utilized, the particles can have the mass of a resting electron, or greater, e.g., 500, 1000, 1500, 2000, 10,000 or even 100,000 times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 amu. Accelerators used to accelerate the particles can be electrostatic DC, electrodynamic DC, RF linear, magnetic induction linear or continuous wave. For example, cyclotron type accelerators are available from IBA, Belgium, such as the Rhodotron® system, while DC type accelerators are available from RDI, now IBA Industrial, such as the Dynamitron®. Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy" Columbus-Ohio, ICRU-IAEA Meeting, 18-20 Mar. 2006, Iwata, Y. et al., "Alternating-Phase-Focused 1H-DTL for Heavy-Ion Medical Accelerators" Proceedings of EPAC 2006, Edinburgh, Scotland and Leaner, C. M. et al., "Status of the Superconducting ECR Ion Source Venus" Proceedings of EPAC 2000, Vienna, Austria.

In some embodiments, a beam of electrons is used as the radiation source. A beam of electrons has the advantages of high dose rates (e.g., 1, 5, or even 10 Mrad per second), high throughput, less containment, and less confinement equipment. Electrons can also be more efficient at causing chain scission. In addition, electrons having energies of 4-10 MeV can have a penetration depth of 5 to 30 mm or more, such as 40 mm. In some cases, multiple electron beam devices (e.g., multiple heads, often referred to as "horns") are used to deliver multiple doses of electron beam radiation to the material. This high total beam power is usually achieved by utilizing multiple accelerating heads. For example, the electron beam device may include two, four, or more accelerating heads. As one example, the electron beam device may include four accelerating heads, each of which has a beam power of 300 kW, for a total beam power of 1200 kW. The use of multiple heads, each of which has a relatively low beam power, prevents excessive temperature rise in the material, thereby preventing burning of the material, and also increases the uniformity of the dose through the thickness of the layer of material. Irradiating with multiple heads is disclosed in U.S. Provisional Application No. 61/394,851, filed Oct. 20, 2010, the complete disclosure of which is incorporated herein by reference.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin piles of materials, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

Electron beam irradiation devices may be procured commercially from Ion Beam Applications, Louvain-la-Neuve, Belgium or the Titan Corporation, San Diego, Calif. Typical electron energies can be 1 MeV, 2 MeV, 4.5 MeV, 7.5 MeV, or 10 MeV. Typical electron beam irradiation device power can be 1 kW, 5 kW, 10 kW, 20 kW, 50 kW, 100 kW, 250 kW, or 500 kW. The level of depolymerization of the feedstock depends on the electron energy used and the dose applied, while exposure time depends on the power and dose. Typical doses may take values of 1 kGy, 5 kGy, 10 kGy, 20 kGy, 50 kGy, 100 kGy, or 200 kGy.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ Hz, greater than $10^{17}$ Hz, $10^{18}$, $10^{19}$, $10^{20}$, or even greater than $10^{21}$ Hz. In some embodiments, the electromagnetic radiation has a frequency of between $10^{18}$ and $10^{22}$ Hz, e.g., between $10^{19}$ to $10^{21}$ Hz.

Doses

In some embodiments, the irradiating (with any radiation source or a combination of sources) is performed until the material receives a dose of at least 0.25 Mrad, e.g., at least 1.0, 2.5, 5.0, 8.0, 10, 15, 20, 25, 30, 35, 40, 50, or even at least 100 Mrad. In some embodiments, the irradiating is performed until the material receives a dose of between 1.0 Mrad and 6.0 Mrad, e.g., between 1.5 Mrad and 4.0 Mrad, 2 Mrad and 10 Mrad, 5 Mrad and 20 Mrad, 10 Mrad and 30 Mrad, 10 Mrad and 40 Mrad, or 20 Mrad and 50 Mrad.

In some embodiments, the irradiating is performed at a dose rate of between 5.0 and 1500.0 kilorads/hour, e.g., between 10.0 and 750.0 kilorads/hour or between 50.0 and 350.0 kilorads/hours.

In some embodiments, two or more radiation sources are used, such as two or more ionizing radiations. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light.

Sonication, Pyrolysis and Oxidation

In addition to radiation treatment, the feedstock may be treated with any one or more of sonication, pyrolysis and oxidation. These treatment processes are described in U.S. Ser. No. 12/417,840, the disclosure of which is incorporated by reference herein.

Other Processes to Solubilize, Reduce Recalcitrance or to Functionalize

Any of the processes of this paragraph can be used alone without any of the processes described herein, or in combination with any of the processes described herein (in any order): steam explosion, chemical treatment (e.g., acid treatment (including concentrated and dilute acid treatment with mineral acids, such as sulfuric acid, hydrochloric acid and organic acids, such as trifluoroacetic acid),) and/or base treatment (e.g., treatment with lime or sodium hydroxide)), UV treatment, screw extrusion treatment (see, e.g., U.S. Patent Application Ser. No. 61/073,530115,398, filed Nov. 1817, 2008), solvent treatment (e.g., treatment with ionic liquids) and freeze milling (see, e.g., U.S. Patent Application Ser. No. 61/081,709).

Production of Fuels, Acids, Esters, and/or Other Products

After one or more of the processing steps discussed above have been performed on the biomass, the complex carbohydrates contained in the cellulose and hemicellulose fractions can be processed into fermentable sugars using a saccharification process, as discussed above.

After the resulting sugar solution has been transported to a manufacturing facility, the sugars can be converted into a variety of products, such as alcohols, e.g., ethanol, or organic acids. The product obtained depends upon the microorganism utilized and the conditions under which the bioprocessing occurs. These steps can be performed, for example, utilizing the existing equipment of the corn-based ethanol manufacturing facility.

The mixing processes and equipment discussed herein may also be used during bioprocessing, if desired. Advantageously, the mixing systems described herein do not impart high shear to the liquid, and do not significantly raise the overall temperature of the liquid. As a result, the microorganisms used in bioprocessing are maintained in a viable condition throughout the process. Mixing may enhance the reaction rate and improve the efficiency of the process.

Generally, fermentation utilizes various microorganisms. The sugar solution produced by saccharification of lignocellulosic materials will generally contain xylose as well as glucose. It may be desirable to remove the xylose, e.g., by chromatography, as some commonly used microorganisms (e.g., yeasts) do not act on xylose. The xylose may be collected and utilized in the manufacture of other products, e.g., animal feeds and the sweetener Xylitol. The xylose may be removed prior to or after delivery of the sugar solution to the manufacturing facility where fermentation will be performed.

The microorganism can be a natural microorganism or an engineered microorganism, e.g., any of the microorganisms discussed in the Materials section herein.

The optimum pH for yeast is from about pH 4 to 5, while the optimum pH for *Zymomonas* is from about pH 5 to 6. Typical fermentation times are about 24 to 96 hours with temperatures in the range of 26° C. to 40° C., however thermophilic microorganisms prefer higher temperatures.

Carboxylic acid groups generally lower the pH of the fermentation solution, tending to inhibit fermentation with some microorganisms, such *Pichia stipitis*. Accordingly, it is in some cases desirable to add base and/or a buffer, before or during fermentation, to bring up the pH of the solution. For example, sodium hydroxide or lime can be added to the fermentation medium to elevate the pH of the medium to range that is optimum for the microorganism utilized.

Fermentation is generally conducted in an aqueous growth medium, which can contain a nitrogen source or other nutrient source, e.g., urea, along with vitamins and trace minerals and metals. It is generally preferable that the growth medium be sterile, or at least have a low microbial load, e.g., bacterial count. Sterilization of the growth medium may be accomplished in any desired manner. However, in preferred implementations, sterilization is accomplished by irradiating the growth medium or the individual components of the growth medium prior to mixing. The dosage of radiation is generally as low as possible while still obtaining adequate results, in order to minimize energy consumption and resulting cost. For example, in many instances, the growth medium itself or components of the growth medium can be treated with a radiation dose of less than 5 Mrad, such as less than 4, 3, 2 or 1 Mrad. In specific instances, the growth medium is treated with a dose of between about 1 and 3 Mrad.

In some embodiments, all or a portion of the fermentation process can be interrupted before the low molecular weight sugar is completely converted to ethanol. The intermediate fermentation products include high concentrations of sugar and carbohydrates. These intermediate fermentation products can be used in preparation of food for human or animal consumption. Additionally or alternatively, the intermediate fermentation products can be ground to a fine particle size in a stainless-steel laboratory mill to produce a flour-like substance.

In some cases the tank can be mobile, as described in U.S. Provisional Patent Application Ser. 60/832,735, now Published International Application No. WO 2008/011598, the full disclosure of which is incorporated herein.

Post-Processing

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Intermediates and Products

Using the processes described herein, the treated biomass can be converted to one or more products, such as energy, fuels, foods and materials. Specific examples of products include, but are not limited to, hydrogen, alcohols (e.g., monohydric alcohols or dihydric alcohols, such as ethanol, n-propanol or n-butanol), hydrated or hydrous alcohols, e.g., containing greater than 10%, 20%, 30% or even greater than 40% water, xylitol, sugars, biodiesel, organic acids (e.g., acetic acid and/or lactic acid), hydrocarbons, co-products (e.g., proteins, such as cellulolytic proteins (enzymes) or single cell proteins), and mixtures of any of these in any combination or relative concentration, and optionally in combination with any additives, e.g., fuel additives. Other examples include carboxylic acids, such as acetic acid or butyric acid, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha, beta unsaturated acids, such as acrylic acid and olefins, such as ethylene. Other alcohols and alcohol derivatives include propanol, propylene glycol, 1,4-butanediol, 1,3-propanediol, methyl or ethyl esters of any of these alcohols. Other products include methyl acrylate, methylmethacrylate, lactic acid, propionic acid, butyric acid, succinic acid, 3-hydroxypropionic acid, a salt of any of the acids and a mixture of any of the acids and respective salts.

Other intermediates and products, including food and pharmaceutical products, are described in U.S. Ser. No. 12/417,900, the full disclosure of which is hereby incorporated by reference herein.

OTHER EMBODIMENTS

A number of embodiments have been described. Nevertheless, it will be understood that various modifications may be made without departing from the spirit and scope of the disclosure.

In some implementations, the systems discussed herein, or components of these systems, may be portable, e.g., in the manner of the mobile processing equipment described in U.S. Ser. No. 12/374,549 and International Application No. WO 2008/011598, the full disclosures of which are incorporated herein by reference.

In any of the dispersing systems described herein, the flow of fluid (liquid and/or gas) through the dispersing system can be continuous or pulsed, or a combination of periods of continuous flow with intervals of pulsed flow. When the flow is pulsed, pulsing can be regular or irregular.

While tanks have been referred to herein, the process may take place in any type of vessel or container, including lagoons, pools, ponds and the like. If the container in which mixing takes place is an in-ground structure such as a lagoon, it may be lined. The container may be covered, e.g., if it is outdoors, or uncovered.

While biomass feedstocks have been described herein, other feedstocks and mixtures of biomass feedstocks with other feedstocks may be used. For example, some implementations may utilize mixtures of biomass feedstocks with hydrocarbon-containing feedstocks such as those disclosed in U.S. Provisional Application No. 61/226,877, filed Jul. 20, 2009, the full disclosure of which is incorporated by reference herein.

Accordingly, other embodiments are within the scope of the following claims.

What is claimed is:

1. A method comprising:
    placing a liquid medium comprising water and at least 20% solids of an unsaccharified electron beam irradiated lignocellulosic feedstock in a vessel;
    mixing the feedstock and water with a jet mixer to form a slurry;
    saccharifying the electron beam irradiated lignocellulosic feedstock in the vessel, while mixing the slurry with the jet mixer, to form a sugar solution, and in the same vessel, converting the sugar solution to a product, utilizing an enzyme and/or a microorganism while continuing to mix with the jet mixer,
    wherein the irradiated lignocellulosic feedstock has been irradiated with a dose of at least 10 Mrad.

2. The method of claim 1 wherein the method further comprises distillation of the product.

3. The method of claim 2 wherein distillation comprises vacuum distillation.

4. The method of claim 3 wherein distillation is performed at a vacuum of less than 70 Torr.

5. The method of claim 3 wherein distillation is performed at ambient temperature.

6. The method of claim 1 wherein the product comprises an alcohol.

7. The method of claim 1 wherein the feedstock has a bulk density of less than about 0.75 g/cm3.

8. The method of claim 1 wherein the liquid medium contains a saccharifying agent that comprises an enzyme.

9. The method of claim 8 further comprising monitoring the glucose level of a mixture of the feedstock, the liquid medium and the saccharifying agent during saccharification.

10. The method of claim 1 further comprising adding additional feedstock and saccharifying agent during saccharification.

11. The method of claim 1 wherein the vessel comprises a tank.

12. The method of claim 1 wherein converting comprises fermentation of the sugar solution.

13. The method of claim 12 further comprising monitoring oxygen level in the vessel during fermentation.

14. The method of claim 1 wherein the sugar solution further comprises xylose.

15. The method of claim 14 further comprising converting xylose to xylitol.

16. The method of claim 1 wherein at least 30% solids of the lignocellulosic material is placed in the vessel.

* * * * *